US011779364B2

(12) United States Patent
Casey et al.

(10) Patent No.: US 11,779,364 B2
(45) Date of Patent: Oct. 10, 2023

(54) ACTUATED EXPANDABLE MOUTH THROMBECTOMY CATHETER

(71) Applicant: NEURAVI LIMITED, Galway (IE)

(72) Inventors: Brendan Casey, Galway (IE); Karl Keating, Galway (IE); Ronald Kelly, Galway (IE); David Vale, Galway (IE)

(73) Assignee: NEURAVI LIMITED, Galway (IE)

( * ) Notice: Subject to any disclaimer, the term of this patent is extended or adjusted under 35 U.S.C. 154(b) by 81 days.

(21) Appl. No.: 17/104,097

(22) Filed: Nov. 25, 2020

(65) Prior Publication Data

US 2021/0153884 A1 May 27, 2021

Related U.S. Application Data

(60) Provisional application No. 62/941,585, filed on Nov. 27, 2019.

(51) Int. Cl.
| | | |
|---|---|---|
| *A61B 17/221* | (2006.01) | |
| *A61B 17/22* | (2006.01) | |
| *A61M 25/01* | (2006.01) | |

(52) U.S. Cl.
CPC ....... *A61B 17/221* (2013.01); *A61M 25/0147* (2013.01); *A61B 2017/2212* (2013.01);
(Continued)

(58) Field of Classification Search
CPC ........ A61B 17/221; A61B 2017/22045; A61B 2017/22084; A61B 2017/2212;
(Continued)

(56) References Cited

U.S. PATENT DOCUMENTS

| 4,243,040 A | 1/1981 | Beecher |
| 4,324,262 A | 4/1982 | Hall |
| | (Continued) | |

FOREIGN PATENT DOCUMENTS

| CN | 1658920 A | 8/2005 |
| CN | 1972728 A | 5/2007 |
| | (Continued) | |

OTHER PUBLICATIONS

US 6,348,062 B1, 02/2002, Hopkins (withdrawn)
(Continued)

*Primary Examiner* — Wade Miles
(74) *Attorney, Agent, or Firm* — TROUTMAN PEPPER HAMILTON SANDERS LLP

(57) ABSTRACT

A clot retrieval catheter can have an expansile distal tip for flow restriction/arrest and improved aspiration efficiency and a large, distal facing mouth into which clots or other obstructions can be retrieved. The tip can be formed from a distal ring of leaflets or hoops. One or more pull cables can be retracted to actuate and radially expand the expansile distal tip. The clot retrieval catheter can have a catheter shaft with flexibility-adding features proximal of the tip. The catheter shaft can be a multi-lumen configuration with a large catheter lumen for passing auxiliary devices and directing aspiration and one or more guide lumens which can route the pull cables to the leaflets or hoops of the expansile tip. A flexible, low-modulus membrane can be disposed around at least a portion of the expansile tip and catheter shaft.

8 Claims, 8 Drawing Sheets

(52) U.S. Cl.
CPC ........... *A61B 2017/2215* (2013.01); *A61B 2017/22045* (2013.01); *A61B 2017/22084* (2013.01)

(58) Field of Classification Search
CPC .. A61B 2017/2215; A61B 2017/22079; A61B 17/22031; A61B 17/320725; A61B 2017/00323; A61B 2017/22072; A61B 2017/320716; A61M 25/0147
See application file for complete search history.

(56) References Cited

U.S. PATENT DOCUMENTS

| | | |
|---|---|---|
| 4,351,342 A | 9/1982 | Wiita et al. |
| 4,575,371 A | 3/1986 | Nordqvist et al. |
| 4,592,356 A | 6/1986 | Gutierrez |
| 4,719,924 A | 1/1988 | Crittenden et al. |
| 4,738,666 A | 4/1988 | Fuqua |
| 4,767,404 A | 8/1988 | Renton |
| 4,793,348 A | 12/1988 | Palmaz |
| 4,873,978 A | 10/1989 | Ginsburg |
| 5,011,488 A | 4/1991 | Ginsburg |
| 5,092,839 A | 3/1992 | Kipperman |
| 5,102,415 A | 4/1992 | Guenther et al. |
| 5,122,136 A | 6/1992 | Guglielmi et al. |
| 5,123,840 A | 6/1992 | Nates |
| 5,171,233 A | 12/1992 | Amplatz |
| 5,234,437 A | 8/1993 | Sepetka |
| 5,256,144 A | 10/1993 | Kraus et al. |
| 5,261,916 A | 11/1993 | Engelson |
| 5,372,124 A | 12/1994 | Takayama et al. |
| 5,385,562 A | 1/1995 | Adams |
| 5,387,219 A | 2/1995 | Rappe |
| 5,387,226 A | 2/1995 | Miraki |
| 5,396,902 A | 3/1995 | Brennen et al. |
| 5,449,372 A | 9/1995 | Schmaltz |
| 5,520,651 A | 5/1996 | Sutcu |
| 5,538,512 A | 7/1996 | Zenzon et al. |
| 5,549,626 A | 8/1996 | Miller et al. |
| 5,558,652 A | 9/1996 | Henke |
| 5,601,600 A | 2/1997 | Ton |
| 5,609,627 A | 3/1997 | Goicoechea et al. |
| 5,624,461 A | 4/1997 | Mariant |
| 5,639,277 A | 6/1997 | Mariant |
| 5,645,558 A | 7/1997 | Horton |
| 5,658,296 A | 8/1997 | Bates |
| 5,662,671 A | 9/1997 | Barbut |
| 5,695,519 A | 12/1997 | Summer et al. |
| 5,709,704 A | 1/1998 | Nott et al. |
| 5,713,853 A | 2/1998 | Clark |
| 5,728,078 A | 3/1998 | Powers, Jr. |
| 5,769,871 A | 6/1998 | Mers Kelly |
| 5,779,716 A | 7/1998 | Cano |
| 5,810,874 A | 9/1998 | Lefebvre |
| 5,814,064 A | 9/1998 | Danniel et al. |
| 5,827,304 A | 10/1998 | Hart |
| 5,846,251 A | 12/1998 | Hart |
| 5,855,598 A | 1/1999 | Pinchuk |
| 5,893,869 A | 4/1999 | Barnhart et al. |
| 5,895,398 A | 4/1999 | Wensel |
| 5,897,567 A | 4/1999 | Ressemann |
| 5,904,698 A | 5/1999 | Thomas et al. |
| 5,911,725 A | 6/1999 | Boury |
| 5,935,139 A | 8/1999 | Bates |
| 5,938,645 A | 8/1999 | Gordon |
| 5,947,995 A | 9/1999 | Samuels |
| 5,968,057 A | 10/1999 | Taheri |
| 5,971,938 A | 10/1999 | Hart et al. |
| 5,997,939 A | 12/1999 | Moechnig et al. |
| 6,022,343 A | 2/2000 | Johnson et al. |
| 6,063,113 A | 5/2000 | Kavteladze |
| 6,066,149 A | 5/2000 | Samson et al. |
| 6,066,158 A | 5/2000 | Engelson |
| 6,093,196 A | 7/2000 | Okada |
| 6,093,199 A | 7/2000 | Brown et al. |
| 6,096,053 A | 8/2000 | Bates |
| 6,099,534 A | 8/2000 | Bates |
| 6,102,932 A | 8/2000 | Kurz |
| 6,106,548 A | 8/2000 | Roubin et al. |
| 6,129,739 A | 10/2000 | Khosravi |
| 6,142,957 A | 11/2000 | Diamond et al. |
| 6,146,396 A | 11/2000 | Kónya et al. |
| 6,146,404 A | 11/2000 | Kim |
| 6,165,194 A | 12/2000 | Denardo |
| 6,165,199 A | 12/2000 | Barbut |
| 6,168,604 B1 | 1/2001 | Cano |
| 6,168,622 B1 | 1/2001 | Mazzocchi |
| 6,174,318 B1 | 1/2001 | Bates et al. |
| 6,179,861 B1 | 1/2001 | Khosravi |
| 6,203,561 B1 | 3/2001 | Ramee |
| 6,214,026 B1 | 4/2001 | Lepak |
| 6,221,006 B1 | 4/2001 | Dubrul |
| 6,238,412 B1 | 5/2001 | Dubrul |
| 6,245,087 B1 | 6/2001 | Addis |
| 6,251,122 B1 | 6/2001 | Tsukernik |
| 6,254,571 B1 | 7/2001 | Hart |
| 6,264,663 B1 | 7/2001 | Cano |
| 6,306,163 B1 | 10/2001 | Fitz |
| 6,309,379 B1 | 10/2001 | Willard |
| 6,312,444 B1 | 11/2001 | Barbut |
| 6,315,778 B1 | 11/2001 | Gambale et al. |
| 6,325,819 B1 | 12/2001 | Pavcnik et al. |
| 6,334,864 B1 | 1/2002 | Amplatz et al. |
| 6,336,934 B1 | 1/2002 | Gilson et al. |
| 6,348,056 B1 | 2/2002 | Bates |
| 6,350,271 B1 | 2/2002 | Kurz et al. |
| 6,361,545 B1 | 3/2002 | Macoviak |
| 6,371,963 B1 | 4/2002 | Nishtala et al. |
| 6,375,668 B1 | 4/2002 | Gifford et al. |
| 6,383,205 B1 | 5/2002 | Samson et al. |
| 6,383,206 B1 | 5/2002 | Gillick |
| 6,391,037 B1 | 5/2002 | Greenhalgh |
| 6,402,771 B1 | 6/2002 | Palmer |
| 6,409,683 B1 | 6/2002 | Fonseca et al. |
| 6,416,541 B2 | 7/2002 | Denardo |
| 6,425,909 B1 | 7/2002 | Dieck et al. |
| 6,432,122 B1 | 8/2002 | Gilson et al. |
| 6,436,112 B2 | 8/2002 | Wensel |
| 6,458,139 B1 | 10/2002 | Palmer |
| 6,346,116 B1 | 11/2002 | Brooks et al. |
| 6,485,497 B2 | 11/2002 | Wensel |
| 6,485,501 B1 | 11/2002 | Green |
| 6,485,502 B2 | 11/2002 | Don Michael |
| 6,511,492 B1 | 1/2003 | Rosenbluth |
| 6,517,551 B1 | 2/2003 | Driskill |
| 6,520,934 B1 | 2/2003 | Lee et al. |
| 6,520,951 B1 | 2/2003 | Carrillo, Jr. |
| 6,530,935 B2 | 3/2003 | Wensel |
| 6,530,939 B1 | 3/2003 | Hopkins |
| 6,540,768 B1 | 4/2003 | Diaz et al. |
| 6,544,279 B1 | 4/2003 | Hopkins |
| 6,551,341 B2 | 4/2003 | Boylan et al. |
| 6,551,342 B1 | 4/2003 | Shen et al. |
| 6,575,997 B1 | 6/2003 | Palmer et al. |
| 6,582,448 B1 | 6/2003 | Boyle |
| 6,585,756 B1 | 7/2003 | Strecker |
| 6,589,265 B1 | 7/2003 | Palmer et al. |
| 6,592,607 B1 | 7/2003 | Palmer et al. |
| 6,592,616 B1 | 7/2003 | Stack |
| 6,602,271 B2 | 8/2003 | Adams |
| 6,602,272 B2 | 8/2003 | Boylan et al. |
| 6,605,102 B1 | 8/2003 | Mazzocchi et al. |
| 6,610,077 B1 | 8/2003 | Hancock et al. |
| 6,616,679 B1 | 9/2003 | Khosravi |
| 6,632,241 B1 | 10/2003 | Hanoock et al. |
| 6,638,245 B2 | 10/2003 | Miller |
| 6,638,293 B1 | 10/2003 | Makower et al. |
| 6,641,590 B1 | 11/2003 | Palmer et al. |
| 6,652,555 B1 | 11/2003 | VanTassel et al. |
| 6,656,218 B1 | 12/2003 | Denardo et al. |
| 6,660,021 B1 | 12/2003 | Palmer et al. |
| 6,663,650 B2 | 12/2003 | Sepetka |
| 6,673,089 B1 | 1/2004 | Yassour et al. |
| 6,685,722 B1 | 2/2004 | Rosenbluth |

(56) References Cited

U.S. PATENT DOCUMENTS

| | | |
|---|---|---|
| 6,692,504 B2 | 2/2004 | Kurz et al. |
| 6,692,508 B2 | 2/2004 | Wensel |
| 6,692,509 B2 | 2/2004 | Wensel |
| 6,702,782 B2 | 3/2004 | Miller |
| 6,712,834 B2 | 3/2004 | Yassour et al. |
| 6,726,701 B2 | 4/2004 | Gilson et al. |
| 6,730,104 B1 | 5/2004 | Sepetka |
| 6,726,703 B2 | 8/2004 | Broome et al. |
| 6,824,545 B2 | 11/2004 | Sepetka |
| 6,855,155 B2 | 2/2005 | Denardo et al. |
| 6,878,163 B2 | 4/2005 | Denardo et al. |
| 6,890,340 B2 | 5/2005 | Duane |
| 6,913,612 B2 | 7/2005 | Palmer |
| 6,913,618 B2 | 7/2005 | Denardo et al. |
| 6,953,472 B2 | 10/2005 | Palmer et al. |
| 6,989,019 B2 | 1/2006 | Mazzocchi |
| 6,989,021 B2 | 1/2006 | Bosma et al. |
| 6,994,718 B2 | 2/2006 | Groothuis et al. |
| 6,997,939 B2 | 2/2006 | Linder |
| 7,004,954 B1 | 2/2006 | Voss et al. |
| 7,004,955 B2 | 2/2006 | Shen |
| 7,004,956 B2 | 2/2006 | Palmer |
| 7,008,434 B2 | 3/2006 | Kurz et al. |
| 7,033,376 B2 | 4/2006 | Tsukernik |
| 7,041,116 B2 | 5/2006 | Goto |
| 7,048,758 B2 | 5/2006 | Boyle |
| 7,058,456 B2 | 6/2006 | Pierce |
| 7,063,707 B2 | 6/2006 | Bose |
| 7,153,320 B2 | 12/2006 | Euteneuer et al. |
| 7,175,655 B1 | 2/2007 | Malaei |
| 7,179,273 B1 | 2/2007 | Palmer et al. |
| 7,220,269 B1 | 5/2007 | Ansel |
| 7,220,271 B2 | 5/2007 | Clubb |
| 7,226,464 B2 | 6/2007 | Garner et al. |
| 7,229,472 B2 | 6/2007 | DePalma et al. |
| 7,232,462 B2 | 6/2007 | Schaeffer |
| 7,288,112 B2 | 10/2007 | Denardo et al. |
| 7,306,618 B2 | 12/2007 | Demond |
| 7,316,692 B2 | 1/2008 | Huffmaster |
| 7,323,001 B2 | 1/2008 | Cubb |
| 7,331,976 B2 | 2/2008 | McGuckin, Jr. et al. |
| 7,344,550 B2 | 3/2008 | Carrison et al. |
| 7,399,308 B2 | 7/2008 | Borillo et al. |
| 7,410,491 B2 | 8/2008 | Hopkins |
| 7,452,496 B2 | 11/2008 | Brady et al. |
| 7,491,215 B2 | 2/2009 | Vale et al. |
| 7,491,216 B2 | 2/2009 | Brady |
| 7,510,565 B2 | 3/2009 | Gilson et al. |
| 7,534,252 B2 | 5/2009 | Sepetka |
| 7,556,636 B2 | 7/2009 | Mazzocchi |
| 7,582,111 B2 | 9/2009 | Krolik et al. |
| 7,594,926 B2 | 9/2009 | Linder |
| 7,604,649 B2 | 10/2009 | McGuckin et al. |
| 7,618,434 B2 | 11/2009 | Santra et al. |
| 7,662,165 B2 | 2/2010 | Gilson et al. |
| 7,670,356 B2 | 3/2010 | Mazzocchi |
| 7,691,121 B2 | 4/2010 | Rosenbluth |
| 7,691,124 B2 | 4/2010 | Balgobin |
| 7,708,770 B2 | 5/2010 | Linder |
| 7,736,385 B2 | 6/2010 | Agnew |
| 7,766,934 B2 | 8/2010 | Pal |
| 7,771,452 B2 | 8/2010 | Pal |
| 7,780,694 B2 | 8/2010 | Palmer |
| 7,780,696 B2 | 8/2010 | Daniel et al. |
| 7,819,893 B2 | 10/2010 | Brady et al. |
| 7,828,815 B2 | 11/2010 | Mazzocchi |
| 7,846,176 B2 | 11/2010 | Mazzocchi |
| 7,846,175 B2 | 12/2010 | Bonnette et al. |
| 7,850,708 B2 | 12/2010 | Pal |
| 7,887,560 B2 | 2/2011 | Kusleika |
| 7,901,426 B2 | 3/2011 | Gilson et al. |
| 7,914,549 B2 | 3/2011 | Morsi |
| 7,922,732 B2 | 4/2011 | Mazzocchi |
| 7,927,349 B2 | 4/2011 | Brady et al. |
| 7,927,784 B2 | 4/2011 | Simpson |
| 7,931,659 B2 | 4/2011 | Bose et al. |
| 7,998,165 B2 | 8/2011 | Huffmaster |
| 8,002,822 B2 | 8/2011 | Glocker et al. |
| 8,021,379 B2 | 9/2011 | Thompson et al. |
| 8,021,380 B2 | 9/2011 | Thompson et al. |
| 8,043,326 B2 | 10/2011 | Hancock et al. |
| 8,048,151 B2 | 11/2011 | O'Brien et al. |
| 8,052,640 B2 | 11/2011 | Fiorella et al. |
| 8,057,497 B1 | 11/2011 | Raju et al. |
| 8,066,757 B2 | 11/2011 | Ferrera et al. |
| 8,070,791 B2 | 12/2011 | Ferrera et al. |
| 8,088,140 B2 | 1/2012 | Ferrera et al. |
| 8,100,935 B2 | 1/2012 | Rosenbluth et al. |
| 8,109,941 B2 | 2/2012 | Richardson |
| 8,118,829 B2 | 2/2012 | Carrison et al. |
| 8,123,769 B2 | 2/2012 | Osborne |
| 8,137,377 B2 | 3/2012 | Palmer |
| 8,142,422 B2 | 3/2012 | Makower et al. |
| 8,142,442 B2 | 3/2012 | Palmer et al. |
| 8,182,508 B2 | 5/2012 | Magnuson et al. |
| 8,187,298 B2 | 5/2012 | Pal |
| 8,246,641 B2 | 8/2012 | Osborne et al. |
| 8,246,672 B2 | 8/2012 | Osborne |
| 8,252,017 B2 | 8/2012 | Paul, Jr. et al. |
| 8,252,018 B2 | 8/2012 | Valaie |
| 8,357,178 B2 | 1/2013 | Grandfield et al. |
| 8,357,179 B2 | 1/2013 | Grandfield et al. |
| 8,357,893 B2 | 1/2013 | Xu et al. |
| 8,361,095 B2 | 1/2013 | Osborne |
| 8,366,663 B2 | 2/2013 | Fiorella et al. |
| 8,372,133 B2 | 2/2013 | Douk et al. |
| 8,382,742 B2 | 2/2013 | Hermann et al. |
| 8,409,215 B2 | 4/2013 | Sepetka et al. |
| 8,419,748 B2 | 4/2013 | Valaie |
| 8,460,312 B2 | 6/2013 | Bose et al. |
| 8,460,313 B2 | 6/2013 | Huffmaster |
| 8,486,104 B2 | 7/2013 | Samson et al. |
| 8,529,596 B2 | 9/2013 | Grandfield et al. |
| 8,574,262 B2 | 11/2013 | Ferrera et al. |
| 8,579,915 B2 | 11/2013 | French et al. |
| 8,585,643 B2 | 11/2013 | Vo et al. |
| 8,585,713 B2 | 11/2013 | Ferrera et al. |
| 8,608,761 B2 | 12/2013 | Osbourne et al. |
| 8,679,142 B2 | 3/2014 | Slee et al. |
| 8,696,622 B2 | 4/2014 | Fiorella et al. |
| 8,702,652 B2 | 4/2014 | Fiorella et al. |
| 8,702,724 B2 | 4/2014 | Olsen et al. |
| 8,784,434 B2 | 7/2014 | Rosenbluth et al. |
| 8,784,441 B2 | 7/2014 | Rosenbluth et al. |
| 8,795,305 B2 | 8/2014 | Grandfield et al. |
| 8,795,317 B2 | 8/2014 | Grandfield et al. |
| 8,795,345 B2 | 8/2014 | Grandfield et al. |
| 8,814,892 B2 | 8/2014 | Galdonik et al. |
| 8,814,925 B2 | 8/2014 | Hilaire et al. |
| 8,900,265 B1 | 12/2014 | Ulm, III |
| 8,939,991 B2 | 1/2015 | Krolick et al. |
| 8,945,143 B2 | 2/2015 | Ferrera et al. |
| 8,945,172 B2 | 2/2015 | Ferrera et al. |
| 8,968,330 B2 | 3/2015 | Rosenbluth et al. |
| 9,039,749 B2 | 5/2015 | Shrivastava et al. |
| 9,072,537 B2 | 7/2015 | Grandfield et al. |
| 9,113,936 B2 | 8/2015 | Palmer et al. |
| 9,119,656 B2 | 9/2015 | Bose et al. |
| 9,138,307 B2 | 9/2015 | Valaie |
| 9,149,609 B2 | 10/2015 | Ansel et al. |
| 9,155,552 B2 | 10/2015 | Ulm, III |
| 9,161,766 B2 | 10/2015 | Slee et al. |
| 9,173,668 B2 | 11/2015 | Ulm, III |
| 9,186,487 B2 | 11/2015 | Dubrul et al. |
| 9,198,687 B2 | 12/2015 | Fulkerson et al. |
| 9,204,887 B2 | 12/2015 | Cully et al. |
| 9,221,132 B2 | 12/2015 | Bowman |
| 9,232,992 B2 | 1/2016 | Heidner |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |

(56) References Cited

U.S. PATENT DOCUMENTS

| | | |
|---|---|---|
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,635 B2 | 5/2017 | Vale et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Paterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 10,028,759 B2 | 7/2018 | Wallace et al. |
| 10,149,692 B2 | 12/2018 | Turjman et al. |
| 10,265,086 B2 | 4/2019 | Vale |
| 10,610,668 B2 | 4/2020 | Burkholz et al. |
| 10,716,915 B2 | 7/2020 | Ogle et al. |
| 10,835,271 B2 | 11/2020 | Ma |
| 11,076,879 B2 | 8/2021 | Yee et al. |
| 2001/0001315 A1 | 5/2001 | Bates |
| 2001/0011182 A1 | 8/2001 | Dubrul et al. |
| 2001/0016755 A1 | 8/2001 | Addis |
| 2001/0041899 A1 | 11/2001 | Foster |
| 2001/0044598 A1 | 11/2001 | Parodi |
| 2001/0044634 A1 | 11/2001 | Don Michael et al. |
| 2001/0051810 A1 | 12/2001 | Dubrul |
| 2002/0002383 A1 | 1/2002 | Sepetka et al. |
| 2002/0016609 A1 | 2/2002 | Wensel |
| 2002/0022859 A1 | 2/2002 | Hogendijk |
| 2002/0026211 A1 | 2/2002 | Khosravi |
| 2002/0049468 A1 | 4/2002 | Streeter |
| 2002/0052620 A1 | 5/2002 | Barvut |
| 2002/0068954 A1 | 6/2002 | Foster |
| 2002/0072764 A1 | 6/2002 | Sepetka |
| 2002/0082558 A1 | 6/2002 | Samson |
| 2002/0091407 A1 | 7/2002 | Zadno-Azizi et al. |
| 2002/0095171 A1 | 7/2002 | Belef |
| 2002/0123765 A1 | 9/2002 | Sepetka |
| 2002/0143362 A1 | 10/2002 | Macoviak et al. |
| 2002/0156455 A1 | 10/2002 | Barbut |
| 2002/0161393 A1 | 10/2002 | Demond |
| 2002/0165576 A1 | 11/2002 | Boyle et al. |
| 2002/0173819 A1 | 11/2002 | Leeflang et al. |
| 2002/0177800 A1 | 11/2002 | Bagaoisan et al. |
| 2002/0188276 A1 | 12/2002 | Evans |
| 2003/0004536 A1 | 1/2003 | Boylan et al. |
| 2003/0004538 A1 | 1/2003 | Secrest |
| 2003/0004542 A1 | 1/2003 | Wensel |
| 2003/0009146 A1 | 1/2003 | Muni |
| 2003/0009191 A1 | 1/2003 | Wensel |
| 2003/0023204 A1 | 1/2003 | Vo et al. |
| 2003/0040769 A1 | 2/2003 | Kelley et al. |
| 2003/0040772 A1 | 2/2003 | Hyodoh et al. |
| 2003/0050663 A1 | 3/2003 | Khachin |
| 2003/0105484 A1 | 6/2003 | Boyle et al. |
| 2003/0125798 A1 | 7/2003 | Matrin |
| 2003/0130682 A1 | 7/2003 | Broome et al. |
| 2003/0144687 A1 | 7/2003 | Brady et al. |
| 2003/0144689 A1 | 7/2003 | Brady et al. |
| 2003/0153940 A1 | 8/2003 | Nohilly et al. |
| 2003/0153943 A1 | 8/2003 | Michael et al. |
| 2003/0153944 A1 | 8/2003 | Phung |
| 2003/0163064 A1 | 8/2003 | Vrba |
| 2003/0163158 A1 | 8/2003 | White |
| 2003/0171769 A1 | 9/2003 | Barbut |
| 2003/0176884 A1 | 9/2003 | Berrada et al. |
| 2003/0187495 A1 | 10/2003 | Cully et al. |
| 2003/0195537 A1 | 10/2003 | Dubrul |
| 2003/0195554 A1 | 10/2003 | Shen |
| 2003/0199917 A1 | 10/2003 | Knudson |
| 2003/0204202 A1 | 10/2003 | Palmer |
| 2003/0212430 A1 | 11/2003 | Bose |
| 2003/0216611 A1 | 11/2003 | Vu |
| 2003/0236533 A1 | 12/2003 | Wilson |
| 2004/0010280 A1 | 1/2004 | Adams et al. |
| 2004/0010282 A1 | 1/2004 | Kusleika |
| 2004/0014002 A1 | 1/2004 | Lundgren |
| 2004/0068288 A1 | 4/2004 | Palmer et al. |
| 2004/0073243 A1 | 4/2004 | Sepetka |
| 2004/0079429 A1 | 4/2004 | Miller |
| 2004/0082962 A1 | 4/2004 | Demarais et al. |
| 2004/0093065 A1 | 5/2004 | Yachia et al. |
| 2004/0133231 A1 | 7/2004 | Maitland |
| 2004/0138692 A1 | 7/2004 | Phung |
| 2004/0153049 A1 | 8/2004 | Hewitt et al. |
| 2004/0153118 A1 | 8/2004 | Clubb |
| 2004/0193107 A1 | 9/2004 | Pierpont et al. |
| 2004/0199202 A1 | 10/2004 | Dubrul et al. |
| 2004/0260333 A1 | 12/2004 | Dubrul et al. |
| 2005/0015047 A1 | 1/2005 | Shah |
| 2005/0020974 A1 | 1/2005 | Noriega |
| 2005/0033348 A1 | 2/2005 | Sepetka |
| 2005/0038447 A1 | 2/2005 | Huffmaster |
| 2005/0038468 A1 | 2/2005 | Panetta et al. |
| 2005/0049619 A1 | 3/2005 | Sepetka |
| 2005/0049669 A1 | 3/2005 | Jones |
| 2005/0049670 A1 | 3/2005 | Jones et al. |
| 2005/0055033 A1 | 3/2005 | Leslie et al. |
| 2005/0055047 A1 | 3/2005 | Greenhalgh |
| 2005/0059993 A1 | 3/2005 | Ramzipoor et al. |
| 2005/0059995 A1 | 3/2005 | Sepetka |
| 2005/0085849 A1 | 4/2005 | Sepetka |
| 2005/0090857 A1 | 4/2005 | Kusleika et al. |
| 2005/0119668 A1 | 6/2005 | Teague et al. |
| 2005/0125024 A1 | 6/2005 | Sepetka |
| 2005/0149111 A1 | 7/2005 | Kanazawa et al. |
| 2005/0171566 A1 | 8/2005 | Kanamaru |
| 2005/0187570 A1 | 8/2005 | Nguyen et al. |
| 2005/0267491 A1 | 8/2005 | Kellett et al. |
| 2005/0216030 A1 | 9/2005 | Sepetka |
| 2005/0216050 A1 | 9/2005 | Sepetka |
| 2005/0288686 A1 | 9/2005 | Sepetka |
| 2005/0228417 A1 | 10/2005 | Teitelbaum et al. |
| 2006/0009785 A1 | 1/2006 | Maitland et al. |
| 2006/0009799 A1 | 1/2006 | Kleshinski et al. |
| 2006/0010636 A1 | 1/2006 | Vacher |
| 2006/0030933 A1 | 2/2006 | DeLeggge et al. |
| 2006/0036271 A1 | 2/2006 | Schomer et al. |

(56) References Cited

U.S. PATENT DOCUMENTS

| | | |
|---|---|---|
| 2006/0058836 A1 | 3/2006 | Bose |
| 2006/0058837 A1 | 3/2006 | Bose |
| 2006/0058838 A1 | 3/2006 | Bose |
| 2006/0064151 A1 | 3/2006 | Guterman et al. |
| 2006/0149313 A1 | 7/2006 | Arguello et al. |
| 2006/0155305 A1 | 7/2006 | Freudenthal |
| 2006/0155322 A1 | 7/2006 | Sater et al. |
| 2006/0161187 A1 | 7/2006 | Levine et al. |
| 2006/0195137 A1 | 8/2006 | Sepetka |
| 2006/0224177 A1 | 10/2006 | Finitsis |
| 2006/0224179 A1 | 10/2006 | Kucharczyk |
| 2006/0229638 A1 | 10/2006 | Abrams et al. |
| 2006/0282111 A1 | 12/2006 | Morsi |
| 2006/0287701 A1 | 12/2006 | Pal |
| 2007/0088383 A1 | 4/2007 | Pal et al. |
| 2007/0142858 A1 | 6/2007 | Bates |
| 2007/0149996 A1 | 6/2007 | Coughlin |
| 2007/0156170 A1 | 7/2007 | Hancock |
| 2007/0165170 A1 | 7/2007 | Fukuda |
| 2007/0191866 A1 | 8/2007 | Palmer et al. |
| 2007/0198028 A1 | 8/2007 | Miloslavski |
| 2007/0198051 A1 | 8/2007 | Clubb et al. |
| 2007/0198075 A1 | 8/2007 | Levy |
| 2007/0208367 A1 | 9/2007 | Fiorella |
| 2007/0208371 A1 | 9/2007 | French |
| 2007/0213765 A1 | 9/2007 | Adams et al. |
| 2007/0225749 A1 | 9/2007 | Martin |
| 2007/0239254 A1 | 10/2007 | Chia et al. |
| 2007/0244505 A1 | 10/2007 | Gilson et al. |
| 2007/0270902 A1 | 11/2007 | Slazas et al. |
| 2007/0288038 A1 | 12/2007 | Bimbo |
| 2007/0293887 A1 | 12/2007 | Okushi et al. |
| 2008/0045881 A1 | 2/2008 | Teitelbaum et al. |
| 2008/0082107 A1 | 4/2008 | Miller et al. |
| 2008/0086190 A1 | 4/2008 | Ta |
| 2008/0091223 A1 | 4/2008 | Pokorney |
| 2008/0097398 A1 | 4/2008 | Mitelberg |
| 2008/0109031 A1 | 5/2008 | Sepetka |
| 2008/0109032 A1 | 5/2008 | Sepetka |
| 2008/0119886 A1 | 5/2008 | Greenhalgh et al. |
| 2008/0177296 A1 | 7/2008 | Sepetka |
| 2008/0183197 A1 | 7/2008 | Sepetka |
| 2008/0183198 A1 | 7/2008 | Sepetka |
| 2008/0183205 A1 | 7/2008 | Sepetka |
| 2008/0188876 A1 | 8/2008 | Sepetka |
| 2008/0188885 A1 | 8/2008 | Sepetka |
| 2008/0188928 A1 | 8/2008 | Salahieh |
| 2008/0200946 A1 | 8/2008 | Braun |
| 2008/0215077 A1 | 9/2008 | Sepetka |
| 2008/0221600 A1 | 9/2008 | Dieck et al. |
| 2008/0228209 A1 | 9/2008 | DeMello et al. |
| 2008/0234706 A1 | 9/2008 | Sepetka |
| 2008/0243170 A1 | 10/2008 | Jenson |
| 2008/0255596 A1 | 10/2008 | Jenson |
| 2008/0262528 A1 | 10/2008 | Martin |
| 2008/0262532 A1 | 10/2008 | Martin |
| 2008/0275488 A1 | 11/2008 | Fleming |
| 2008/0275493 A1 | 11/2008 | Farmiga |
| 2008/0281350 A1 | 11/2008 | Sepetka |
| 2008/0312681 A1 | 12/2008 | Ansel |
| 2009/0024157 A1 | 1/2009 | Anukhin |
| 2009/0054918 A1 | 2/2009 | Henson |
| 2009/0069828 A1 | 3/2009 | Martin |
| 2009/0076539 A1 | 3/2009 | Valaie |
| 2009/0105722 A1 | 4/2009 | Fulkerson |
| 2009/0105737 A1 | 4/2009 | Fulkerson |
| 2009/0131908 A1 | 5/2009 | McKay |
| 2009/0163846 A1 | 5/2009 | Aklog et al. |
| 2009/0177206 A1 | 7/2009 | Lozier et al. |
| 2009/0182336 A1 | 7/2009 | Brenzel et al. |
| 2009/0221967 A1 | 9/2009 | Thommen et al. |
| 2009/0270815 A1 | 10/2009 | Stamp et al. |
| 2009/0281610 A1 | 11/2009 | Parker |
| 2009/0292297 A1 | 11/2009 | Ferrere |
| 2009/0292307 A1 | 11/2009 | Razack |
| 2009/0299374 A1 | 12/2009 | Tilson et al. |
| 2009/0299393 A1 | 12/2009 | Martin |
| 2009/0306702 A1 | 12/2009 | Miloslavski |
| 2010/0004607 A1 | 1/2010 | Wilson et al. |
| 2010/0016957 A1 | 1/2010 | Jager et al. |
| 2010/0030186 A1 | 2/2010 | Stivland |
| 2010/0030256 A1 | 2/2010 | Dubrul et al. |
| 2010/0036312 A1 | 2/2010 | Krolik et al. |
| 2010/0087908 A1 | 4/2010 | Hilaire |
| 2010/0114017 A1 | 5/2010 | Lenker |
| 2010/0125326 A1 | 5/2010 | Kalstad |
| 2010/0125327 A1 | 5/2010 | Agnew |
| 2010/0191272 A1 | 7/2010 | Keating |
| 2010/0211094 A1 | 8/2010 | Sargent, Jr. |
| 2010/0249815 A1 | 9/2010 | Jantzen et al. |
| 2010/0268264 A1 | 10/2010 | Bonnett et al. |
| 2010/0268265 A1 | 10/2010 | Krolik et al. |
| 2010/0292726 A1 | 11/2010 | Olsen et al. |
| 2010/0305566 A1 | 12/2010 | Rosenblatt et al. |
| 2010/0305604 A1 | 12/2010 | Pah |
| 2010/0318178 A1 | 12/2010 | Rapaport et al. |
| 2010/0324649 A1 | 12/2010 | Mattsson |
| 2010/0331949 A1 | 12/2010 | Habib |
| 2011/0009875 A1 | 1/2011 | Grandfield et al. |
| 2011/0009940 A1 | 1/2011 | Grandfield et al. |
| 2011/0009942 A1 | 1/2011 | Gregorich |
| 2011/0022149 A1 | 1/2011 | Cox et al. |
| 2011/0054514 A1 | 3/2011 | Arcand |
| 2011/0054516 A1 | 3/2011 | Keegan |
| 2011/0060359 A1 | 3/2011 | Hannes |
| 2011/0071432 A1 | 3/2011 | Carrillo, Jr. et al. |
| 2011/0077620 A1 | 3/2011 | deBeer |
| 2011/0098683 A1 | 4/2011 | Wiita et al. |
| 2011/0054504 A1 | 5/2011 | Wolf et al. |
| 2011/0125181 A1 | 5/2011 | Brady et al. |
| 2011/0130756 A1 | 6/2011 | Everson, Jr. et al. |
| 2011/0152920 A1 | 6/2011 | Eckhouse et al. |
| 2011/0160763 A1 | 6/2011 | Ferrera et al. |
| 2011/0166586 A1 | 7/2011 | Sepetka et al. |
| 2011/0196414 A1 | 8/2011 | Porter et al. |
| 2011/0202088 A1 | 8/2011 | Eckhouse et al. |
| 2011/0213290 A1 | 9/2011 | Chin et al. |
| 2011/0213297 A1 | 9/2011 | Aklog et al. |
| 2011/0213393 A1 | 9/2011 | Aklog et al. |
| 2011/0213403 A1 | 9/2011 | Aboytes |
| 2011/0218564 A1 | 9/2011 | Drasler et al. |
| 2011/0224707 A1 | 9/2011 | Miloslavski et al. |
| 2011/0264132 A1 | 10/2011 | Strauss et al. |
| 2011/0276120 A1 | 11/2011 | Gilson et al. |
| 2011/0319917 A1 | 12/2011 | Ferrera et al. |
| 2012/0041449 A1 | 2/2012 | Eckhouse et al. |
| 2012/0041474 A1 | 2/2012 | Eckhouse et al. |
| 2012/0059356 A1 | 3/2012 | diPama et al. |
| 2012/0089216 A1 | 4/2012 | Rapaport et al. |
| 2012/0101510 A1 | 4/2012 | Lenker et al. |
| 2012/0116351 A1 | 5/2012 | Chomas et al. |
| 2012/0116440 A1 | 5/2012 | Leynov et al. |
| 2012/0143237 A1 | 6/2012 | Cam et al. |
| 2012/0143239 A1 | 6/2012 | Aklog et al. |
| 2012/0150147 A1 | 6/2012 | Leynov et al. |
| 2012/0165858 A1 | 6/2012 | Eckhouse et al. |
| 2012/0165859 A1 | 6/2012 | Eckhouse et al. |
| 2012/0215250 A1 | 8/2012 | Grandfield et al. |
| 2012/0277788 A1 | 11/2012 | Cattaneo |
| 2012/0283768 A1 | 11/2012 | Cox et al. |
| 2012/0296362 A1 | 11/2012 | Cam et al. |
| 2012/0316600 A1 | 12/2012 | Ferrera et al. |
| 2013/0006284 A1 | 1/2013 | Aggerholm et al. |
| 2013/0030461 A1* | 1/2013 | Marks et al. |
| 2013/0046330 A1 | 2/2013 | McIntosh et al. |
| 2013/0046333 A1 | 2/2013 | Jones et al. |
| 2013/0046334 A1 | 2/2013 | Jones et al. |
| 2013/0116774 A1 | 5/2013 | Strauss et al. |
| 2013/0131614 A1 | 5/2013 | Hassan et al. |
| 2013/0144326 A1 | 6/2013 | Brady et al. |
| 2013/0144328 A1 | 6/2013 | Weber et al. |
| 2013/0158592 A1 | 6/2013 | Porter |
| 2013/0184703 A1 | 7/2013 | Shireman et al. |
| 2013/0184739 A1 | 7/2013 | Brady et al. |

(56) References Cited

U.S. PATENT DOCUMENTS

| | | |
|---|---|---|
| 2013/0197567 A1 | 8/2013 | Brady et al. |
| 2013/0226146 A1 | 8/2013 | Tekulve |
| 2013/0268050 A1 | 10/2013 | Wilson et al. |
| 2013/0281788 A1 | 10/2013 | Garrison |
| 2013/0289697 A1 | 10/2013 | Baker et al. |
| 2013/0325055 A1 | 12/2013 | Eckhouse et al. |
| 2013/0325056 A1 | 12/2013 | Eckhouse et al. |
| 2013/0345739 A1 | 12/2013 | Brady et al. |
| 2014/0012281 A1 | 1/2014 | Wang et al. |
| 2014/0046359 A1 | 2/2014 | Bowman et al. |
| 2014/0052097 A1 | 2/2014 | Petersen et al. |
| 2014/0081243 A1 | 3/2014 | Zhou et al. |
| 2014/0121672 A1 | 5/2014 | Folk |
| 2014/0128905 A1 | 5/2014 | Molaei |
| 2014/0135812 A1 | 5/2014 | Divino et al. |
| 2014/0180377 A1 | 6/2014 | Bose et al. |
| 2014/0188127 A1 | 7/2014 | Dubrul et al. |
| 2014/0194919 A1 | 7/2014 | Losardo et al. |
| 2014/0200607 A1 | 7/2014 | Sepetka et al. |
| 2014/0200608 A1 | 7/2014 | Brady et al. |
| 2014/0236220 A1 | 8/2014 | Inoue |
| 2014/0257018 A1 | 9/2014 | Farnan |
| 2014/0257362 A1 | 9/2014 | Eldenschink |
| 2014/0276922 A1 | 9/2014 | McLain et al. |
| 2014/0277003 A1 | 9/2014 | Hendrick |
| 2014/0277053 A1 | 9/2014 | Wang et al. |
| 2014/0277079 A1 | 9/2014 | Vale et al. |
| 2014/0309657 A1 | 10/2014 | Ben-Ami |
| 2014/0309673 A1 | 10/2014 | Dacuycuy et al. |
| 2014/0330302 A1 | 11/2014 | Tekulve et al. |
| 2014/0343585 A1 | 11/2014 | Ferrera et al. |
| 2014/0364896 A1 | 12/2014 | Consigny |
| 2014/0371769 A1 | 12/2014 | Vale et al. |
| 2014/0371777 A1 | 12/2014 | Rudakov et al. |
| 2014/0371779 A1 | 12/2014 | Vale et al. |
| 2014/0371780 A1 | 12/2014 | Vale et al. |
| 2014/0379023 A1 | 12/2014 | Brady et al. |
| 2015/0018859 A1 | 1/2015 | Quick et al. |
| 2015/0018860 A1 | 1/2015 | Quick et al. |
| 2015/0080937 A1 | 3/2015 | Davidson |
| 2015/0081003 A1 | 3/2015 | Wainwright et al. |
| 2015/0112376 A1 | 4/2015 | Molaei et al. |
| 2015/0133990 A1 | 5/2015 | Davidson |
| 2015/0142043 A1 | 5/2015 | Furey |
| 2015/0164523 A1 | 6/2015 | Brady et al. |
| 2015/0173782 A1 | 6/2015 | Garrison et al. |
| 2015/0173783 A1* | 6/2015 | Tah et al. |
| 2015/0238314 A1 | 8/2015 | Börtlein et al. |
| 2015/0250497 A1 | 9/2015 | Marks et al. |
| 2015/0257775 A1 | 9/2015 | Gilvarry et al. |
| 2015/0258270 A1 | 9/2015 | Kunis |
| 2015/0297252 A1 | 10/2015 | Miloslavski et al. |
| 2015/0306311 A1 | 10/2015 | Pinchuk et al. |
| 2015/0313617 A1 | 11/2015 | Grandfield et al. |
| 2015/0320431 A1 | 11/2015 | Ulm, III |
| 2015/0351770 A1 | 12/2015 | Fulton, III |
| 2015/0352325 A1 | 12/2015 | Quick |
| 2015/0359547 A1 | 12/2015 | Vale et al. |
| 2015/0374391 A1 | 12/2015 | Quick et al. |
| 2015/0374393 A1 | 12/2015 | Brady et al. |
| 2015/0374479 A1 | 12/2015 | Vale |
| 2016/0015402 A1 | 1/2016 | Brady et al. |
| 2016/0022296 A1 | 1/2016 | Brady et al. |
| 2016/0066921 A1 | 3/2016 | Brady et al. |
| 2016/0074067 A1 | 3/2016 | Furnish et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0120558 A1 | 5/2016 | Brady et al. |
| 2016/0121080 A1 | 5/2016 | Cottone |
| 2016/0135829 A1 | 5/2016 | Holochwost et al. |
| 2016/0143653 A1 | 5/2016 | Vale et al. |
| 2016/0346002 A1* | 5/2016 | Avneri et al. |
| 2016/0151079 A1 | 6/2016 | Aklog et al. |
| 2016/0192953 A1 | 7/2016 | Brady et al. |
| 2016/0192954 A1 | 7/2016 | Brady et al. |
| 2016/0192955 A1 | 7/2016 | Brady et al. |
| 2016/0192956 A1 | 7/2016 | Brady et al. |
| 2016/0228134 A1 | 8/2016 | Martin et al. |
| 2016/0256180 A1 | 9/2016 | Vale et al. |
| 2016/0262880 A1 | 9/2016 | Li et al. |
| 2016/0317168 A1 | 11/2016 | Brady et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0065401 A1 | 3/2017 | Fearnot et al. |
| 2017/0071614 A1 | 3/2017 | Vale et al. |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086862 A1 | 3/2017 | Vale et al. |
| 2017/0086863 A1 | 3/2017 | Brady et al. |
| 2017/0086864 A1 | 3/2017 | Greenhalgh et al. |
| 2017/0086996 A1 | 3/2017 | Peterson et al. |
| 2017/0239447 A1 | 3/2017 | Greenhalgh et al. |
| 2017/0095138 A1 | 4/2017 | Nakade et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0105743 A1 | 4/2017 | Vale et al. |
| 2017/0112515 A1 | 4/2017 | Brady et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172554 A1 | 6/2017 | Bortlein et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0238953 A1 | 8/2017 | Yang et al. |
| 2017/0252043 A1 | 9/2017 | Fuller et al. |
| 2017/0252064 A1 | 9/2017 | Staunton |
| 2017/0259042 A1 | 9/2017 | Nguyen et al. |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Sethna |
| 2017/0290654 A1 | 10/2017 | Sethna |
| 2017/0296324 A1 | 10/2017 | Argentine |

(56) References Cited

U.S. PATENT DOCUMENTS

| | | |
|---|---|---|
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0008407 A1 | 1/2018 | Maimon et al. |
| 2018/0042623 A1 | 2/2018 | Batiste |
| 2018/0193050 A1 | 7/2018 | Hawkins et al. |
| 2018/0193591 A1 | 7/2018 | Jaroch et al. |
| 2018/0235743 A1 | 8/2018 | Farago et al. |
| 2018/0256177 A1 | 9/2018 | Cooper et al. |
| 2018/0303610 A1 | 10/2018 | Anderson |
| 2019/0021755 A1 | 1/2019 | Johnson et al. |
| 2019/0021759 A1 | 1/2019 | Krolik et al. |
| 2019/0029820 A1 | 1/2019 | Zhou et al. |
| 2019/0029825 A1 | 1/2019 | Fitterer et al. |
| 2019/0046219 A1 | 2/2019 | Marchand et al. |
| 2019/0192175 A1 | 6/2019 | Chida et al. |
| 2019/0209206 A1 | 7/2019 | Patel et al. |
| 2019/0216476 A1 | 7/2019 | Barry et al. |
| 2019/0239907 A1 | 8/2019 | Brady et al. |
| 2019/0247627 A1 | 8/2019 | Korkuch et al. |
| 2019/0255290 A1 | 8/2019 | Snyder et al. |
| 2019/0269491 A1 | 9/2019 | Jalgaonkar et al. |
| 2019/0274810 A1 | 9/2019 | Phouasalit et al. |
| 2019/0298396 A1 | 10/2019 | Gamba et al. |
| 2019/0365411 A1 | 12/2019 | Avneri et al. |
| 2019/0366049 A1 | 12/2019 | Hannon et al. |
| 2020/0038628 A1 | 2/2020 | Chou et al. |
| 2020/0214859 A1 | 7/2020 | Sherburne |
| 2020/0281611 A1 | 9/2020 | Kelly et al. |
| 2020/0353208 A1 | 11/2020 | Merhi et al. |
| 2020/0383698 A1 | 12/2020 | Miao et al. |
| 2021/0085935 A1 | 3/2021 | Fahey et al. |
| 2021/0153883 A1 | 5/2021 | Casey et al. |
| 2021/0153884 A1 | 5/2021 | Casey et al. |
| 2021/0154433 A1 | 5/2021 | Casey et al. |
| 2021/0219821 A1 | 7/2021 | Appling et al. |
| 2022/0117614 A1 | 4/2022 | Salmon et al. |
| 2022/0125450 A1 | 4/2022 | Sirhan et al. |
| 2022/0313426 A1 | 10/2022 | Gifford, III et al. |
| 2023/0054898 A1 | 2/2023 | Gurovich et al. |

FOREIGN PATENT DOCUMENTS

| | | |
|---|---|---|
| CN | 103071195 A | 5/2013 |
| CN | 104507380 A | 4/2015 |
| CN | 104905873 A | 9/2015 |
| CN | 105007973 A | 10/2015 |
| CN | 105307582 A | 2/2016 |
| CN | 105726163 A | 7/2016 |
| CN | 106232059 A | 12/2016 |
| CN | 113040865 A | 6/2021 |
| DE | 20 2009 001 951 U1 | 4/2010 |
| DE | 10 2009 056 450 A1 | 6/2011 |
| DE | 10 2010 010 849 A1 | 9/2011 |
| DE | 10 2010 014 778 A1 | 10/2011 |
| DE | 10 2010 024 085 A1 | 12/2011 |
| DE | 10 2011 014 586 B3 | 9/2012 |
| DE | 20 2020 107013 U1 | 1/2021 |
| EP | 2301450 A1 | 3/2011 |
| EP | 2628455 A1 | 8/2013 |
| EP | 3302312 A1 | 4/2018 |
| EP | 3335647 A2 | 6/2018 |
| EP | 3 420 978 A1 | 1/2019 |
| EP | 4049704 A2 | 8/2022 |
| GB | 2498349 A | 7/2013 |
| JP | 9-19438 A | 1/1997 |
| WO | WO 93/04722 A2 | 3/1993 |
| WO | 94/24926 A1 | 11/1994 |
| WO | 97/27808 A1 | 8/1997 |
| WO | 97/38631 A1 | 10/1997 |
| WO | 99/20335 A1 | 4/1999 |
| WO | 99/56801 A2 | 11/1999 |
| WO | 99/60933 A1 | 12/1999 |
| WO | 01/21077 A1 | 3/2001 |
| WO | 02/02162 A2 | 1/2002 |
| WO | 02/11627 A2 | 2/2002 |
| WO | 02/43616 A2 | 6/2002 |
| WO | 02/070061 A1 | 9/2002 |
| WO | 02/094111 A2 | 11/2002 |
| WO | 03/002006 A1 | 1/2003 |
| WO | 03/018085 A2 | 3/2003 |
| WO | 03/030751 A1 | 4/2003 |
| WO | 03/051448 A2 | 6/2003 |
| WO | 2004/028571 A1 | 4/2004 |
| WO | 2004/056275 A1 | 7/2004 |
| WO | 2005/000130 A1 | 1/2005 |
| WO | 2005/027779 A2 | 3/2005 |
| WO | WO 2005/027751 A1 | 3/2005 |
| WO | 2006/021407 A2 | 3/2006 |
| WO | 2006/031410 A2 | 3/2006 |
| WO | 2006/107641 A2 | 10/2006 |
| WO | 2006/135823 A2 | 12/2006 |
| WO | 2007/054307 A2 | 5/2007 |
| WO | 2007/068424 A2 | 6/2007 |
| WO | 2008/034615 A2 | 3/2008 |
| WO | 2008/051431 A1 | 5/2008 |
| WO | 2008/131116 A1 | 10/2008 |
| WO | 2009/019664 A1 | 2/2009 |
| WO | 2009/031338 A1 | 3/2009 |
| WO | 2009/076482 A1 | 6/2009 |
| WO | 2009/086482 A2 | 7/2009 |
| WO | 2009/105710 A1 | 8/2009 |
| WO | WO 2009/103125 A1 | 8/2009 |
| WO | 2010/010545 A1 | 1/2010 |
| WO | 2010/046897 A1 | 4/2010 |
| WO | 2010/075565 A1 | 7/2010 |
| WO | 2010/102307 A1 | 9/2010 |
| WO | 2010/146581 A1 | 12/2010 |
| WO | 2011/013556 A1 | 2/2011 |
| WO | 2011/066961 A1 | 6/2011 |
| WO | 2011/082319 A1 | 7/2011 |
| WO | 2011/095352 A1 | 8/2011 |
| WO | 2011/106426 A1 | 9/2011 |
| WO | 2011/110316 A1 | 9/2011 |
| WO | 2012/052982 A1 | 4/2012 |
| WO | 2012/064726 A1 | 5/2012 |
| WO | 2012/081020 A1 | 6/2012 |
| WO | 2012/110619 A1 | 8/2012 |
| WO | 2012/120490 A2 | 9/2012 |
| WO | 2012/156924 A1 | 11/2012 |
| WO | 2013/016435 A1 | 1/2013 |
| WO | 2013/072777 A2 | 5/2013 |
| WO | 2013/105099 A2 | 7/2013 |
| WO | 2013/109756 A2 | 7/2013 |
| WO | 2014/081892 A1 | 5/2014 |
| WO | 2014/139845 A1 | 9/2014 |
| WO | 2014/169266 A1 | 10/2014 |
| WO | 2014/178198 A1 | 11/2014 |
| WO | WO 2014/188300 A1 | 11/2014 |
| WO | 2015/061365 A1 | 4/2015 |
| WO | 2015/134625 A1 | 9/2015 |
| WO | 2015/179324 A1 | 11/2015 |
| WO | WO 2015/179377 A1 | 11/2015 |
| WO | 2015/189354 A1 | 12/2015 |
| WO | 2016/010995 A1 | 1/2016 |
| WO | WO 2017/004234 A1 | 1/2017 |
| WO | WO 2017/097616 A1 | 6/2017 |
| WO | 2018/193603 A1 | 10/2018 |
| WO | WO 2018/178979 A1 | 10/2018 |

(56) References Cited

FOREIGN PATENT DOCUMENTS

| WO | WO 2019/064306 A1 | 4/2019 |
| WO | WO 2019/079296 A1 | 4/2019 |
| WO | WO 2020/139979 A1 | 7/2020 |
| WO | WO 2021/016213 A1 | 1/2021 |
| WO | WO 2021/167653 A1 | 8/2021 |
| WO | WO 2022/020366 A2 | 1/2022 |

OTHER PUBLICATIONS

Struffert, T., et al. "Intravenous flat detector CT angiography for non-invasive visualisation of intracranial flow diverter: technical feasibility" Eur Radiol 21:1797-1801 (2011).
Extended European Search Report dated Jul. 28, 2021 issued in European Patent Application No. 20 21 0069.

\* cited by examiner

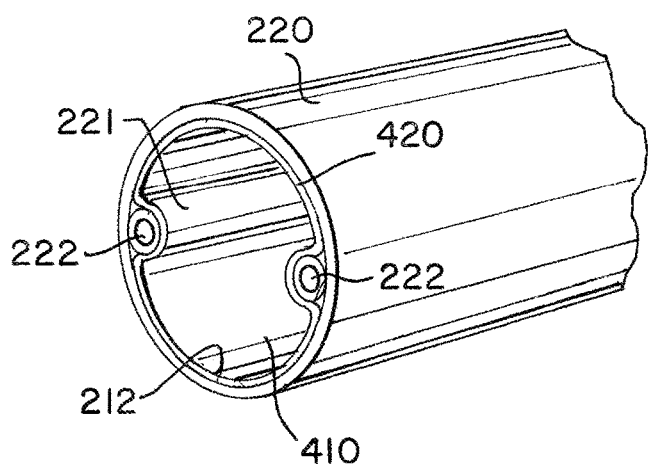
FIG. 12b
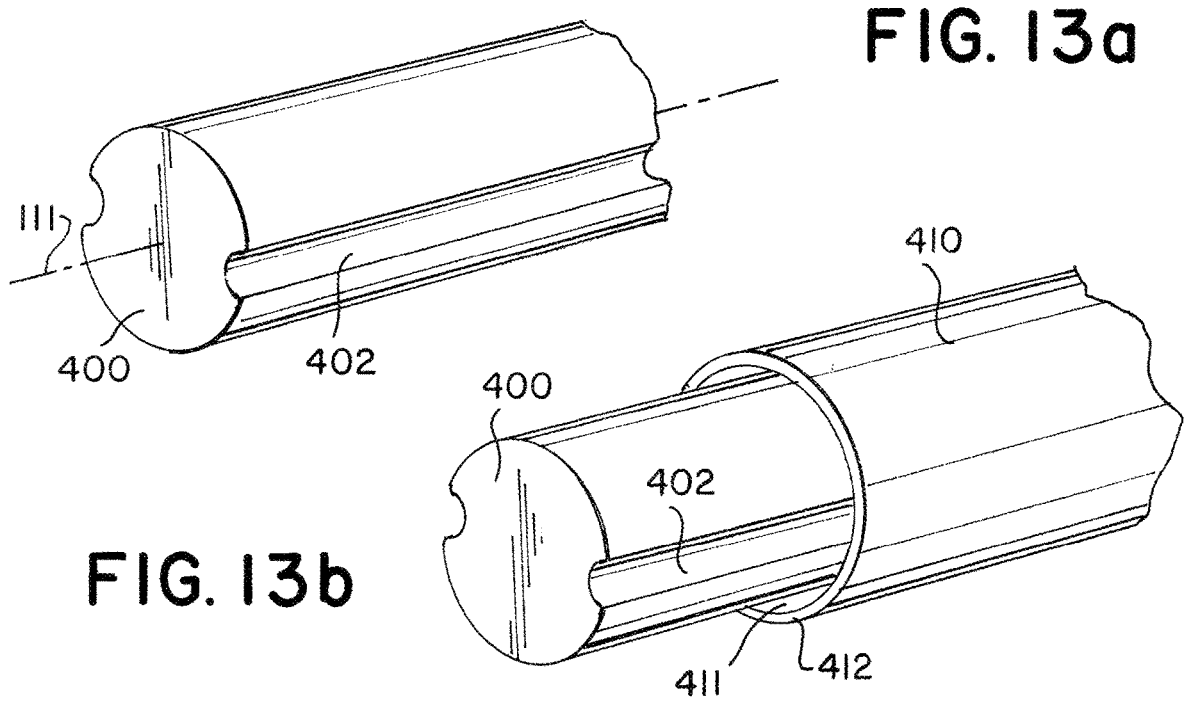
FIG. 13a
FIG. 13b
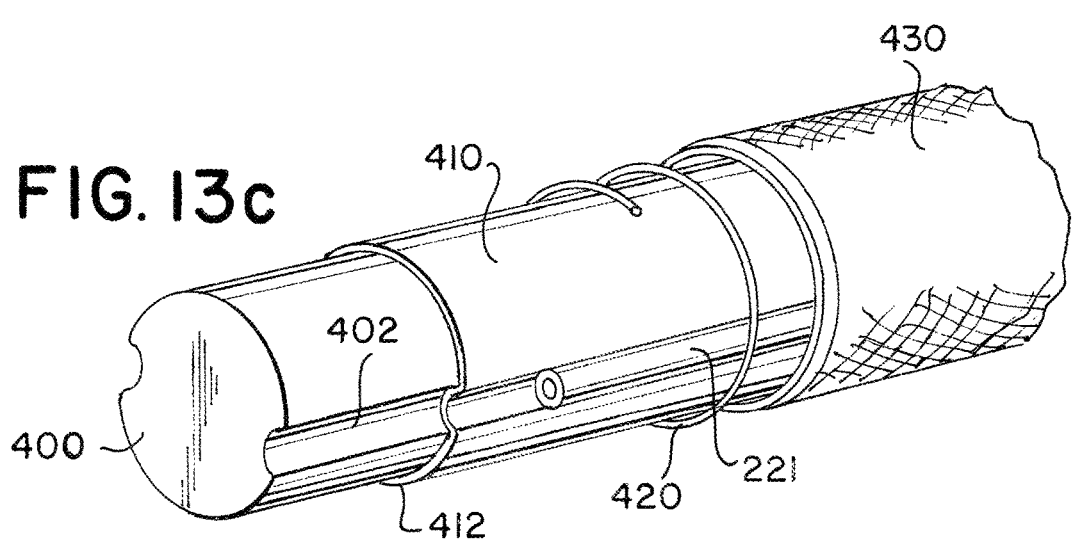
FIG. 13c

ACTUATED EXPANDABLE MOUTH THROMBECTOMY CATHETER

CROSS-REFERENCE TO RELATED APPLICATION

The present application claims the benefit of priority of U.S. Provisional Patent Application No. 62/941,585, filed on Nov. 27, 2019 and incorporated herein by reference in its entirety.

FIELD OF INVENTION

The present invention generally relates devices and methods for removing acute blockages from blood vessels during intravascular medical treatments. More specifically, the present invention relates to retrieval catheters with expandable tips into which an object or objects can be retrieved.

BACKGROUND

Clot retrieval catheters and devices are used in mechanical thrombectomy for endovascular intervention, often in cases where patients are suffering from conditions such as acute ischemic stroke (AIS), myocardial infarction (MI), and pulmonary embolism (PE). Accessing the neurovascular bed in particular is challenging with conventional technology, as the target vessels are small in diameter, remote relative to the site of insertion, and are highly tortuous. Traditional devices are often either too large in profile, lack the deliverability and flexibility needed to navigate tortuous vessels, or are not effective at removing a clot when delivered to the target site.

The clot itself can complicate procedures by taking on a number of complex morphologies and consistencies, ranging from simple tube-shaped structures which assume the shape of the vessel to long, strand-like arrangements that can span multiple vessels at one time. The age of a clot can also affect its compliance, with older clots tending to be less compressible than fresh clots. Experience has also demonstrated that depending on the nature of the interaction with a clot retrieval device, the mechanical properties of a clot can be affected in a significant way. Additionally, several mechanisms play a role in strongly adhering the clot to the vessel wall. Breaking these bonds without damaging fragile vessels is a significant challenge.

The delivery of effective devices to the small and highly-branched cerebral artery system remains challenging, and conventional clot retrieval catheters suffer from a number of drawbacks. First, the diameters of catheters themselves must be small enough to avoid causing significant discomfort to the patient. The retrieval catheter must also be sufficiently flexible to navigate the vasculature and endure high strains, while also having the axial stiffness to offer smooth advancement along the route. Once at the target site, typical objects to be retrieved from the body are substantially larger in size than the catheter tip diameter, making it more difficult to retrieve objects into the tip. For example, firm, fibrin-rich clots can often be difficult to extract as they can become lodged in the tip of traditional fixed-mouth catheters. Additionally, this lodging can cause other softer portions to shear away from the firmer regions of the clot.

Small diameters and fixed tip sizes are also less efficient at directing the aspiration necessary to remove blood and thrombus material during the procedure. The suction must be strong enough such that any fragmentation that may occur as a result of aspiration or the use of a mechanical thrombectomy device cannot migrate and occlude distal vessels. However, when aspirating with a fixed-mouth catheter, a significant portion of the aspiration flow ends up coming from vessel fluid proximal to the tip of the catheter, where there is no clot. This significantly reduces aspiration efficiency, lowering the success rate of clot removal.

Many catheter designs have therefore been put forth with a mouth that can be expanded at a target site. When a clot is captured and drawn proximally into a tip with a funnel shape, the clot can be progressively compressed during retrieval so that it can be aspirated filly through the catheter and into an aspiration syringe or cannister. In addition, if a clot does become lodged in the funnel shape of the tip, the expanded mouth can protect the clot and prevent it from dislodging as the aspiration suction is maintained and the catheter is retracted into a guide catheter or outer sheath.

However, any catheter design attempting to overcome the above-mentioned design challenges with an expanding distal tip or funnel structure would need to have the strength to grip the clot and exert a steady radial force in the expanded state. The same structure would also need to have the flexibility and elasticity to survive the severe mechanical strains imparted when navigating the tortuous vasculature in a collapsed state. The tip would also require a means for the user to actuate expansion in a consistent and repeatable manner when deployed from an access or intermediate catheter, balloon guide catheter, or other such sheath.

The present designs are aimed at providing an improved retrieval catheter with an expansile tip which incorporates these features to address the above-stated deficiencies.

SUMMARY

The designs herein can be for a clot retrieval catheter capable of providing local flow restriction/arrest within the target vessel, while also having a large clot-facing mouth. The catheter can be sufficiently flexible so as to be capable of navigating highly tortuous areas of the anatomy, such as the neurovascular, to reach an occlusive clot. The catheter can also be compatible with relatively low-profile access sheaths and catheters for deliverability advantages.

The clot retrieval catheter may have a substantially tubular body with one or more internal lumens extending therethrough. A large central catheter lumen can be configured for the passage of guidewires, microcatheters, stent retrievers, and other such devices therethrough. The lumen can also direct aspiration to an expansile tip at the distal end of the catheter. The tubular body can terminate at a distal end, at which the expansile tip can be integrally-formed or fixedly connected. The tip can be configured to expand from a collapsed delivery configuration to an expanded deployed configuration when extended from the access or intermediate catheter at the site of an occlusive thrombus. The expansion can be activated by a user with controls on a proximal handle of the catheter.

In some examples, the tubular body can have a series of loop ribs extending laterally to and at various lengths from one or more axially-extending longitudinal spines. The ribs and spines can be monolithically formed though laser machining or extrusion of a polymeric tube. In another example, the tubular body can be of metallic braid or coiled wire construction covered with or impregnated within a polymeric jacket. The spine can be fixedly connected to, or formed integrally with, a part of the expansile tip.

The expansile tip disposed at the distal end of the catheter body can be actuated by a user to assume the radially expanded deployed configuration. The tip can be actuated by control members such as pull cables, which can be tensioned or pushed by the user and be distally connected to the one or more members of the expansile tip. The pull wires can be constructed of steel or a high-modulus polymer with enough axial stiffness so that both tensioning and pushing of the wires actuates functions of the tip. One or more pull cable guide tubes can be disposed around the circumference of the catheter body and can run the length of the catheter axis. Each guide tube can have an internal tubular lumen sized to allow uninhibited relative motion of the pull cable. The pull wire guide tubes can be tangent to either the internal or external wall of the support tube, or they can be formed mid-wall.

In some examples, the guide tubes can terminate at a point proximal to the distal end of the tubular catheter shaft, be flush with the distal end of the shaft, or further extend a distance distal to the distal end shaft. A distal cutaway can also be machined or formed approximate the distal end of the catheter shaft and/or guide tubes to allow for a more gradual, shallow expansion angle for the pull cables relative to the longitudinal axis. A proximal control handle or luer can allow the pull cables to be tensioned together, such that a uniform and consistent radial expansion is imparted around the circumference of the expansile tip.

In the expanded deployed configuration, the tip can assume a substantially conical or funnel shape in which struts form a plurality of leaflets or distal hoops around the longitudinal axis which can define an open, distal-facing mouth for retrieval of occlusions. The leaflets can have distal peaks with a gently sloping loop or petal shape for atraumatic contact with the walls of a vessel when expanded. The leaflets can also overlap with each other circumferentially such that adjacent leaflets are capable of relative sliding motion with respect to each other. This configuration can give the tip enhanced flexibility by allowing twisting or bending motions in tortuous areas of the vasculature. Overlapping leaflets can also enable the tip to fold upon itself for low-profile deliverability and when the tip is collapsed back into an outer sheath or catheter. The leaflets may or may not be axisymmetric with the longitudinal axis of the catheter. The struts forming the leaflets can connect at the distal end of the tubular body, and the struts may be aligned with one of the one or more axial spines of the support tube.

In some examples, the plurality of leaflets can have one or more actuated leaflets and one or more passive leaflets. The actuated and passive leaflets can have a distal peak and one or more proximal joints connected to the catheter shaft. Each of the one or more actuated leaflets can be connected to a pull cable for actuating and expanding the expansile tip.

The connections between the pull wires and leaflets can have a variety of configurations such that the tip maintains some lateral flexibility at the joints. The pull wires can be connected to the leaflets through a number of means. In one configuration, one or more tensioning members extend proximally from distal peaks of actuated leaflets and terminate in an eyelet. Pull cables extending distally from the guide tubes of the catheter body can terminate in enlarged bulbs at their distalmost ends which extend through the eyelets such that the pull cables and the struts of the leaflets are coupled but not rigidly connected. When bending, or when the tip is placed under compressive loads during retrieval of a clot, fewer rigid connections can give the tip added flexibility and the ability to deflect locally for a tighter grip on the captured clot.

In other examples, the bulbs can be of a polygonal or non-spherical shape such that other designs tailoring the bending stiffness of the interface between the expansile tip and catheter body can be anticipated. A further design can have a flexible hinged joint, such as a pinned connection between the leaflet struts and the pull cables extending distally from the guide tubes of the catheter body. A hinged joint can define or bias certain bending planes for the catheter while being delivered.

In some examples, at least a portion of the leaflets can contain patterns which would increase flexibility, such as undulations or expandable cells. In one example, the leaflet struts can have a waveform shape or have narrowed sections to improve the overall flexibility tip structure.

The proximal joints of the leaflets can also be designed in multiple ways to reduce stresses and increase the flexibility of the tip. In the catheter shaft is cut from a hypotube, the leaflets could be formed integrally at the distal end of the shaft. In another example, additional lateral flexibility can be gained by cutting anchoring slots approximate the distal end of the catheter shaft configured to axially constrain leaflet anchors forming the proximal joints of the leaflets. The leaflets can be longitudinally anchored within the anchoring slots. The slots can be machined through the wall of the catheter body to form a restraining structure for anchors of the leaflets. The leaflets can extend distally, and each leaflet can overlap with one or more adjacent leaflets to form a flexible petal-like arrangement. The struts of adjacent leaflets can cross over and be capable of relative motion such that the tip is not constrained when deploying to, or collapsing from, the expanded deployed configuration. In this configuration, the pull cables extending through the catheter body can form a loop around adjacent leaflets at the crossover points where the leaflets overlap. The pull cable loops can engage cross over points 180 degrees apart so that tensioning of the pull cables can result in smooth and uniform deployment of the tip.

A flexible cover can be disposed to form a sleeve around at least a part of the support tube and at least a part of the strut framework of the expansile tip. The cover can be a membrane formed from a ductile elastomer, which has the advantages of being soft and flexible with resistance to tearing and perforation due to a high failure strain. As an alternative, the cover can be one or more polymer jackets which can be fused together and adhered, reflowed, or stitched to encapsulate at least part of the tip. The membrane can further be coated with or be made from an elastomer or similar material to provide a low-friction surface to facilitate navigation within blood vessels as well as other catheters.

In another example, a thrombectomy catheter can have a tubular catheter shaft and an expansile tip integrally formed at the distal end of the catheter shaft. The catheter shaft can have a distal end and a catheter lumen with a longitudinal axis intending therethrough. In some examples, the catheter shaft can have one or more pull cable guide tubes disposed about the circumference of the catheter lumen. The guide tubes can house one or more pull cables disposed within pull cable lumens in the guide tubes and capable of being operably tensioned by a user of the catheter using a proximal handle. In one case, two pull cables can be spaced 180 degrees apart around the circumference of the catheter shaft.

The expansile tip can be integrally formed at the distal end of the catheter shaft. The tip and shaft can be formed from a single polymeric extrusion or metallic tube. The extrusion can be, for instance, fabricated from polyether ether ketone (PEEK) or another rugged thermoplastic polymer. The extrusion can also be laser cut with transverse and/or axial slots to increase the flexibility of the tube. In one example, the expansile tip can have a plurality of leaflets configured to radially expand from a collapsed delivery configuration to an expanded deployed configuration when the one or more pull cables are tensioned. The expansile tip can be at least partially encapsulated by one or more outer jackets.

In one more specific example, the plurality of leaflets can be two actuated leaflets connected to the pull cables and two passive leaflets joined circumferentially to the actuated leaflets. The actuated leaflets can be configured to actuate the expansile tip between the collapsed delivery configuration and the expanded deployed configuration when the pull cables are tensioned.

The size and shape of the passive and actuated leaflets can be designed to guide the folding and expansion of the expansile tip. The passive leaflets can have a substantially horseshoe shaped profile. The actuated and passive leaflets can be a similar size. Alternatively, the actuated leaflets can be significantly larger than the passive leaflets, such that they make up a substantially larger portion of the expansile tip. In some examples, the actuated leaflets can make up the majority of the circumference of the tip and shaped to shortens and widens as the tip flares outwards when the pull cables are retracted. This motion of the actuated leaflets can help the passive leaflets flare outward rather than just stretching between the actuated leaflets.

In a further example, a thrombectomy catheter can have a tubular catheter shaft with a distal end and a catheter lumen with a longitudinal axis intending therethrough. A sliding collar can be disposed around the catheter shaft and be configured to slide telescopically along the longitudinal axis. In some examples, one or more pull cables can be fixedly connected to the sliding collar and disposed about the circumference of the catheter lumen. The pull cables can be capable of being operably tensioned by a user of the catheter to slide the sliding collar along the catheter shaft.

The thrombectomy catheter can also have an expansile tip approximate the distal end of the catheter shaft. The tip can have a collapsed delivery configuration and a radially expanded deployed configuration. In some examples the tip can have a plurality of circumferentially overlapping distal hoops around the longitudinal axis. The hoops can be configured to form a funnel profile when the expansile tip is in the expanded deployed configuration. In other examples, one or more outer jackets can at least partially encapsulate the expansile tip.

In some cases, the hoops can be extensions from a braided wire support structure of the catheter shaft so that there is no abrupt stiffness transition between the catheter body and the tip. In another example, the leaflets can be formed with a braided configuration where adjacent leaflets are woven or intertwined at some distance proximal of the distal end of the tip. In a similar example, the wire leaflets of the expansile tip can be formed independently from the reinforcing wire braid of the catheter body so the tip and the catheter shaft are separate sections. In this configuration the proximal ends of the leaflets can be anchored in the circumferential sliding collar disposed around the catheter body.

The distal hoops can be actuated to expand the expansile tip in a number of ways. In one example, the pull cables can be connected directly to distal peaks of the hoops. When the cables are tensioned, the overlapping hoops can flare radially outward together, similar to a fan. In another example, the distal hoops can connect at their proximal ends to the sliding collar such that they radially expand as the pull cables are tensioned and the collar slides telescopically along the catheter shaft. In a further example, the one or more outer jackets encapsulating the hoops of the tip can be connected proximally to the sliding collar such that the jackets and hoops are radially expanded as the pull cables are tensioned.

For the designs disclosed, the catheter shaft can have a composite construction which can include an inner layer having low-friction liner such as PTFE and a thick strike layer bonded to the low-friction liner. This layer can be assembled as a sleeve over a mandrel having one or more longitudinal grooves and conformed to the shape of the outer surface of the mandrel. The inner layer can assume the shape of the longitudinal grooves of the mandrel and can form circumferential support for one or more pull wire guide lumens when the guide tubing is inserted into the grooves. A coil or braided reinforcing layer can then be disposed around the outer diameter of the inner layer. By changing the axial spacings of the coil or braid can give variable stiffness properties to different axial lengths of the catheter shaft. A membrane cover can be applied and laminated or fused to the structure. When bonded, the mandrel can be removed to open the inner catheter lumen.

Other aspects and features of the present disclosure will become apparent upon reviewing the following detailed description in conjunction with the accompanying figures.

Additional features or manufacturing steps can be included as would be appreciated and understood by a person of ordinary skill in the art.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIG. 12*b* is an end view of a composite catheter shaft construction according to aspects of the present invention;

FIGS. 13a-13d illustrate steps for the construction of a composite catheter shaft according to aspects of the present invention;

DETAILED DESCRIPTION

Specific examples of the present invention are now described in detail with reference to the Figures, where identical reference numbers indicate elements which are functionally similar or identical. The figures illustrate a thrombectomy catheter with an expansile distal tip. The mouth of the tip can be formed from a distal ring of members. One or more pull cables can be retracted to actuate and expand the distal ring of members to a deployed condition. The tip can radially expand to seal with the walls of the vessel, restricting flow and blocking fluid proximal of the tip so more efficient aspiration can be directed distally to dislodge and capture a clot. The catheter shaft can have a multi-lumen configuration with a central catheter lumen for the passage of ancillary devices and directing aspiration and one or more guide lumens which can route the pull cables to the expansile tip. A flexible, low-modulus membrane can be disposed around at least a portion of the expansile tip and catheter shaft.

The objective of the disclosed designs is to create a clot retrieval catheter capable of providing both local flow restriction/arrest and a large clot facing mouth. This catheter can be capable of navigating the tortuous neurovascular to reach an occlusive clot and can therefore be highly flexible. The catheter can also be compatible with relatively low-profile access sheaths and catheters, so that a puncture wound in the patient's groin (in the case of femoral access) can be easily and reliably closed. The clot retrieval catheter can pass through a sheath or guide with an inner diameter of less than 0.110", preferably 0.090", in some cases less than 0.087", and most preferably less than 0.085". Therefore, the catheter and expansile tip can be capable of a low delivery profile, of approximately 0.084" or 2 mm, and yet be able to expand its distal mouth to the size of the vessel in which the clot is located, which could be as large as 5 mm. The pull cables allow an operator to control the diameter of the tip at discrete times during a procedure. Disclosed designs can also allow the user to collapse the tip during or after the procedure.

Accessing the various vessels within the vascular, whether they are coronary, pulmonary, or cerebral, involves well-known procedural steps and the use of a number of conventional, commercially-available accessory products. These products, such as angiographic materials, rotating hemostasis valves, mechanical thrombectomy devices, and guidewires are widely used in laboratory and medical procedures. When these products are employed in conjunction with the system and methods of this invention in the description below, their function and exact constitution are not described in detail. While the description is in many cases in the context of thrombectomy treatments, the systems and methods may be adapted for other procedures and in other body passageways as well.

Figure 1:
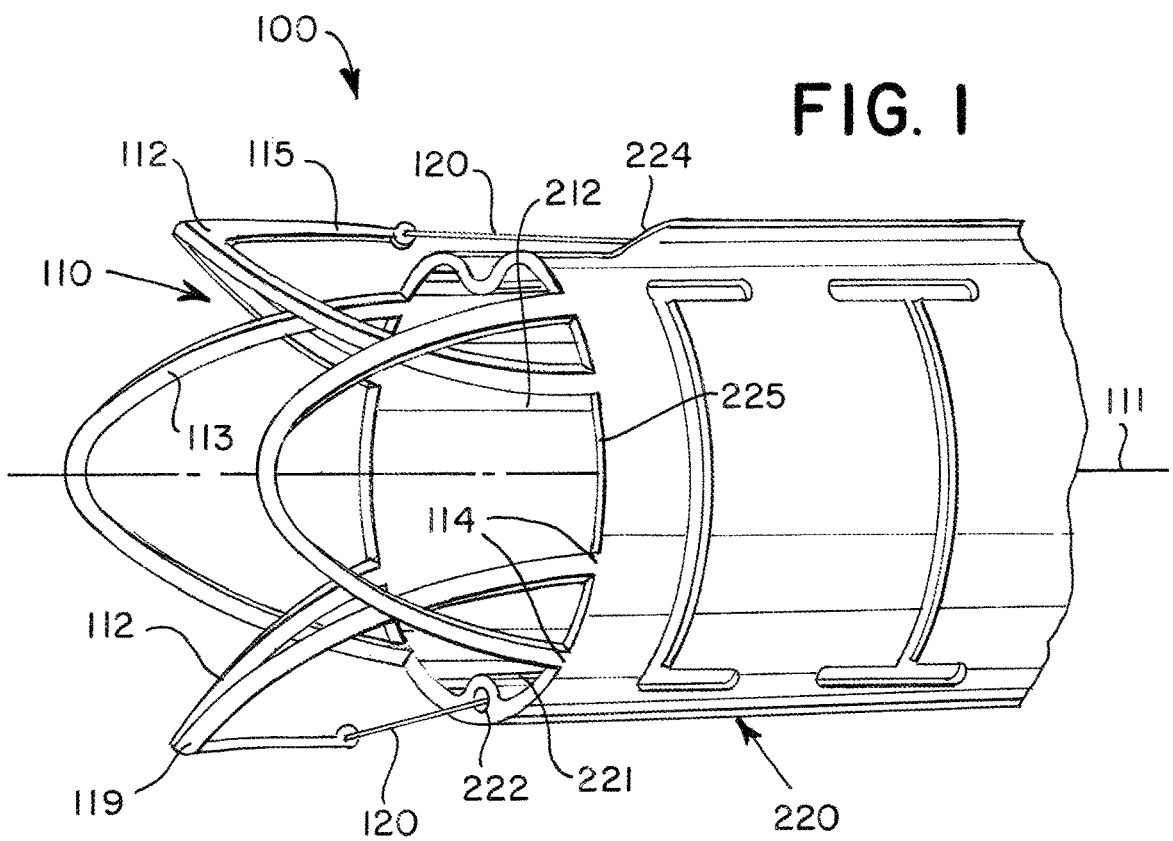
FIG. 1 is a view of a clot retrieval catheter with an expansile tip according to aspects of the present invention.

Turning to the figures, FIG. 1 illustrates the distal portion of a clot retrieval catheter 100 having a proximal catheter shaft 220 and a distal expansile tip 110. The catheter 100 can be navigated to a target site in the vascular using standard interventional techniques and commercially available ancillary devices such as an access catheter, balloon guide catheter, and/or guidewires. The catheter shaft body 220 can have a generally tubular structure disposed around a longitudinal axis 111.

In one configuration, the tip 110 can have multiple leaflets 112, 113 forming an expandable petal shape when unfolded from the collapsed delivery configuration. The leaflets can be struts or wires configured into the shape of a loop or hoop. The example shown in FIG. 1 includes two actuation leaflets 112 and two passive leaflets 113 rigidly connected to the distal end 225 of the catheter shaft 220. The two actuation leaflets 112 can be positioned 180 degrees apart and circumferentially overlap with the struts of the two passive leaflets 113.

The number of actuated and passive leaflets can vary based on the needs of the device. For example, increasing the number of leaflets can increase the support for a membrane and the radial force for sealing with a vessel wall, but will also increase the lateral stiffness of the tip for a given strut thickness and width.

In some instances, the leaflets 112, 113 can contain patterns which would increase flexibility, such as undulations, narrowed sections, or expandable cells. Undulations in the leaflets can aid the tip shortening and lengthening at opposite sides in a collapsed delivery configuration when being advanced through tortuous vessels to a target site. Furthermore, undulations can help prevent one or more leaflets or portions of the tip from overextending if the catheter 100 is pushed distally while the tip 110 is expanded. In other examples the leaflets 112, 113 can have a low taper angle and curve radially inward at the distal end when expanded so the struts do not press into the vessel walls.

The expansile tip 110 can be fixedly or flexibly coupled at proximal joints 114 to the distal end 225 of the catheter shaft 220 and configured to radially expand from a collapsed delivery configuration within an outer sheath or catheter to a radially-expanded deployed configuration. FIG. 1 shows fixed leaflet proximal joints 114. It can be appreciated that the leaflets can also be connected via a more flexible linkage, such as eyelets. The leaflets can also have features such as narrowed sections or notches which can serve as hinge points for uniform and consistent expansion and folding of the tip 110.

The catheter shaft 220 can be a multi-lumen system having a primary catheter lumen 212 and one or more guide tubes 221 defining guide lumens 222. The catheter lumen 212 can be used for the delivery of auxiliary devices, such as microcatheters and stentrievers, and can also be used to direct aspiration distally through the expansile tip 110. The structure of the shaft 220 can be, for example, a polymer and/or metal braid support structure with an internal low friction liner and outer polymer jacket or jackets that can be reflowed into the braid structure during manufacturing.

The guide tubes 221 can extend axially parallel to the longitudinal axis 111 from a proximal luer or control handle (not shown) manipulated by the user. The guide tubes can terminate distally approximate the distal end 225 of the catheter shaft 220, or proximal or distal to the distal end. The guide tubes 221 can serve as conduits for control members or pull wires cables 120 configured to expand and/or collapse the expansile tip 110.

The outer surface of the catheter shaft 220 and expansile tip 110 can be at least partially covered by a membrane or outer jacket or jackets (not shown). The membrane or jackets can block proximal fluid from entering the tip during aspiration and retrieval of the clot, allowing for more efficient direction of the aspiration force while preventing the distal migration of clot fragments of other debris during the procedure. In one example, the jacket or jackets can be formed from a highly-elastic material such that the radial force exerted by expanding the expansile tip is sufficient to stretch the membrane to the funnel or conical shape contours of the tip when in the expanded deployed configuration. Alternately, the jackets can be baggy and loose and fold over the leaflets so that the leaflets can move freely. A baggy jacket folded from the inner diameter to the outer diameter of the tip 110 can have the inner and outer surfaces adhered or heat welded together between leaflet struts to reduce the strain required to expand the jacket and strengthen the resistance of the inner portion of the membrane from collapsing under aspiration.

Figure 2A:
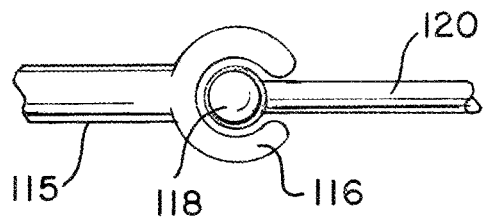
FIGS. 2*a-c* show alternate examples of connecting the pull cables to the expansile tip from FIG. 1 according to aspects of the present invention.
Figure 2B:
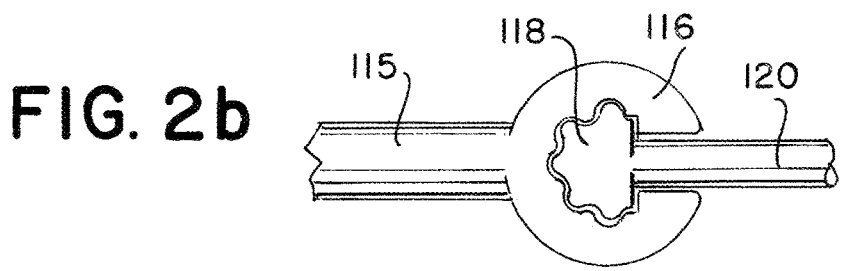
Figure 2C:
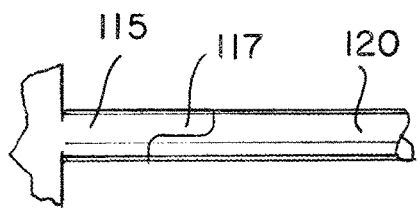

FIGS. 2a-2c show various methods of flexible attachment joints between the actuated leaflets 112 of the expansile tip 110 and the pull cables 120. The pull cables 120 can be constructed of steel or a large molecular weight polymer with sufficient tensile strength to cause the expansion deflections of the tip 110 when actuated by the user. The pull cables 120 aid in providing a smooth transition during the expansion or retraction of the expansile tip and can be spaced circumferentially to balance the passive leaflets 113 which may not be directly coupled to the support tube of the catheter shaft 220. For example, by having two actuated leaflets 112 spaced 180 degrees apart, such as the configuration in FIG. 1, the tip 110 can bend about the bending plane of the two cables 120 when being advanced to or withdrawn from a target.

The pull cable 120 members can be secured in place with an enlarged bulb ends 118 at their distalmost ends as shown in FIGS. 2a and 2b. The bulb ends 118 can be formed during manufacturing after the pull cables 120 had been fed through associated eyelets 116 formed on the expansile tip. The eyelets can be located at the proximal ends of tensioning members 115 extending proximally of actuated tip leaflets 112. The bulb 118 can be formed by any of a number of methods, such as forming a knot, applying heat, laser cutting, molding, or with mechanical plastic deformation. In another example, eyelets 116 can be loops formed at the junction of adjacent leaflets 112.

In another example, the bulbs can be of a polygonal or non-spherical shape such that they can still be retained by the eyelet 116 while transmitting bending moments to the leaflets 112, 113 without a rigidly configured joint in all degrees of freedom. Other designs tailoring the bending stiffness of the interface between the expansile tip and catheter body can be anticipated. FIG. 2c shows a further design which can have a flexible hinged joint where a hinge link 117 forms at the overlapping interface between a pull cable 120 and a tensioning member 115 of an actuation leaflet 112. The hinge link 117 can be a single or dual pinned connection defining one or more bending planes for the expansile tip 110. A circumferentially-aligned dual pinned connection, for example, would provide the tip with flexibility in two planes perpendicular to each other while maintaining support for the tip from all of the leaflets. The hinged joint can also be a universal joint to open more degrees of freedom for the tip 110 to flex.

Figure 3:
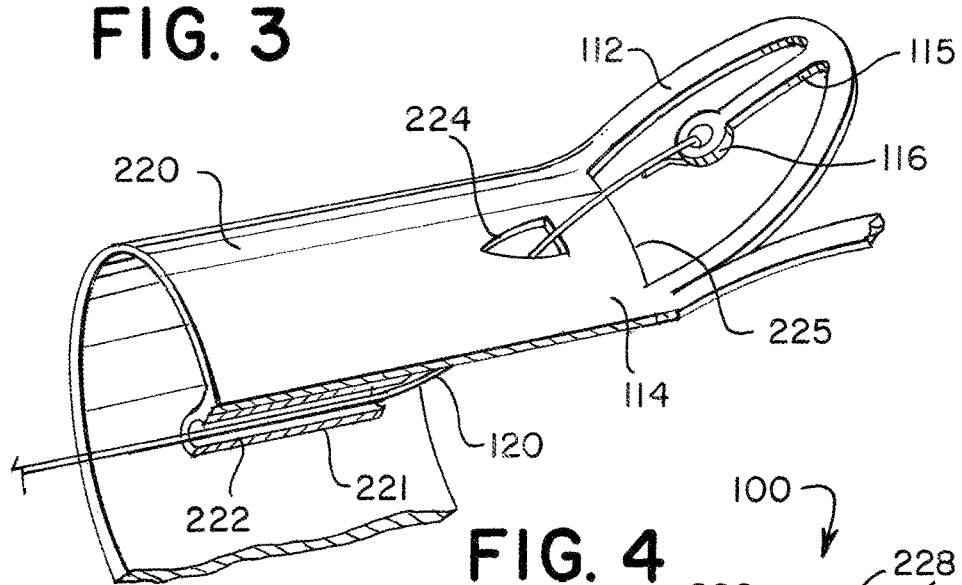
FIG. 3 shows an alternate arrangement to change the angle at which the pull cable can actuate the expansile tip according to aspects of the present invention.

The pull cables 120 can exit the guide lumens 222 at the distal end 225 of the catheter shaft 220 or the shaft and guide tubes 221 can have a fillet or scallop forming a distal cutaway 224 in the outer surface of the shaft, as illustrated in FIG. 3. The distal cutaway 224 can alter the angle of pull exerted by the pull cable 120 on the tensioning member 115 by allowing a shallower exit angle from the cable lumen 222. The cutaway 224 can be located at a specific distance proximal of the distal end 225 of the catheter shaft 220 to fix the exit angle as shown. In another example, the cutaway can be a slot extending a distance proximal to the distal end 225. In a further example, individual pull cables 120 can be split to exit two or more distal cutaways 224 in the catheter shaft 220 so as to pull more than one of the actuated leaflets 112 around the circumference to the expansile tip 110 using a single pull cable 120.

The pull cables 120 should be able to move very freely within the guide lumens 222 along the axis 111 of the catheter shaft 220. A low-friction system could be utilized using materials such as PTFE or FEP for the lining of the guide lumens 222, and/or the outer surface of the pull cables 120. Alternately, a lubricant (such as silicone oil or molybdenum disulfide) could also be used, or a coating such as a hydrophilic coating. The pull cables themselves can be made of a very high-modulus material, so that a thin, low-profile cable can be used which exhibits minimal stretch or elongation when under tension in use. Metallics such stainless steel, Nitinol or MP35N could also be used when the pull cables are in a wire or multifilament cable form. Engineering polymers or composites such as UHMWPE, LCP, Vectran or Kevlar can also be envisaged as suitable materials. In addition, combinations of both a wire and cable and/or both a metal and polymer could also be used. For example, a solid Nitinol wire with a PTFE coating can be used for the majority of the pull cable, with a short segment of UHMWPE near the distal end to aid in connecting the pull cable to the actuated leaflets 112 of the expansile tip 110. A proximal solid monofilament can also be used to provide good pushability and column stiffness in the pull cable so that it can be advanced to collapse the frame if desired.

Figure 4:
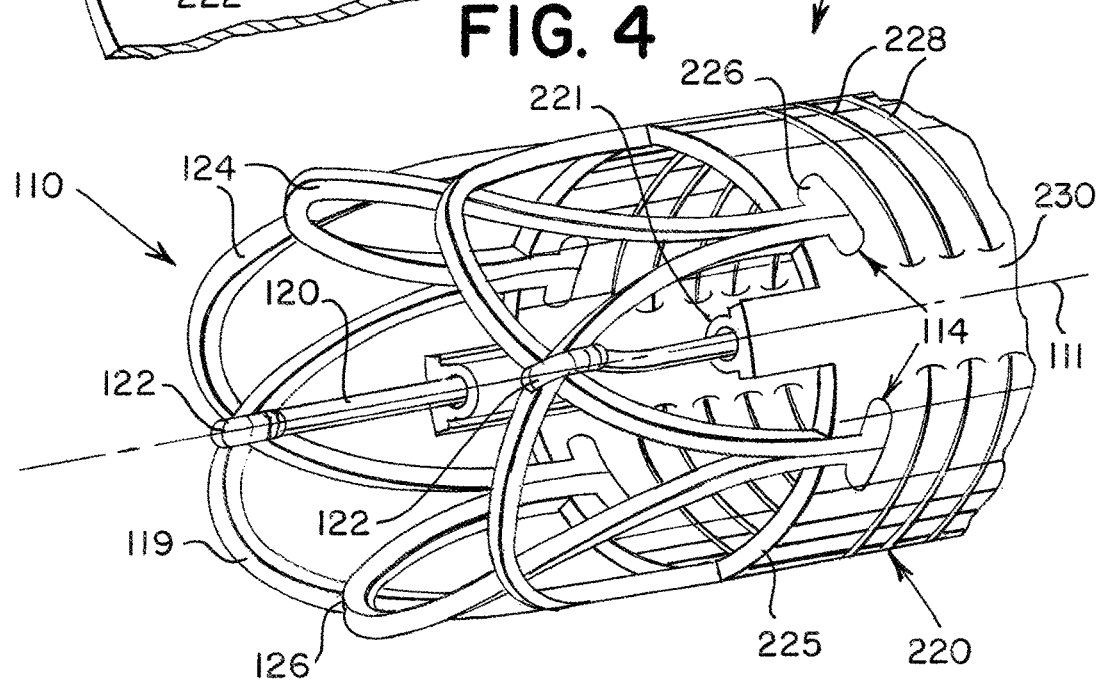
FIG. 4 shows an alternative catheter example according to aspects of the present invention.

In another configuration shown in FIG. 4, the catheter 100 can have a tubular catheter shaft 220 configured around a longitudinal axis 111. The catheter shaft 220 can have longitudinal and/or transverse cuts 228 machined into the surface at regular or variable spacings so that the flexibility of the catheter 100 can be tailored along its length. For example, the slots can be sized or spaced to give the proximal portion of the catheter greater pushability and trackability characteristics. Differing slot spacing along a more distal length of the shaft 220 can allow for more flexibility for the narrow and tortuous vessels near an occlusive clot.

The catheter shaft 220 shown can have two guide tubes 221 spaced 180 degrees apart on opposing sides of the shaft circumference. The guide tubes 221 can be used for the routing of pull cables 120 for actuating the expansion and collapse of the distal expansile tip 110. The guide tubes 221 can extend the full length of the catheter shaft and circumferentially interrupt the transverse cuts or slots 228 in the shaft to form longitudinally extending spines 230. The axial spines 230 can have a constant thickness or can be tapered to provide a smooth stiffness transition between the proximal and distal portions of the catheter shaft 220.

Figure 5:
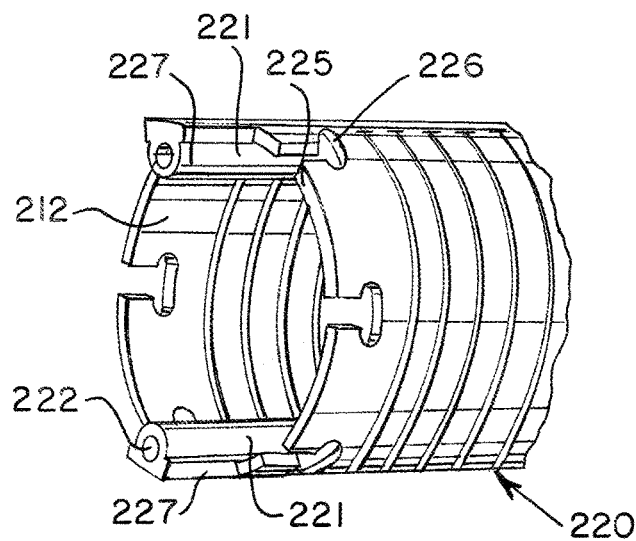
FIG. 5 is a view of a possible construction of the shaft from the example in FIG. 4 according to aspects of the present invention.
Figure 6:
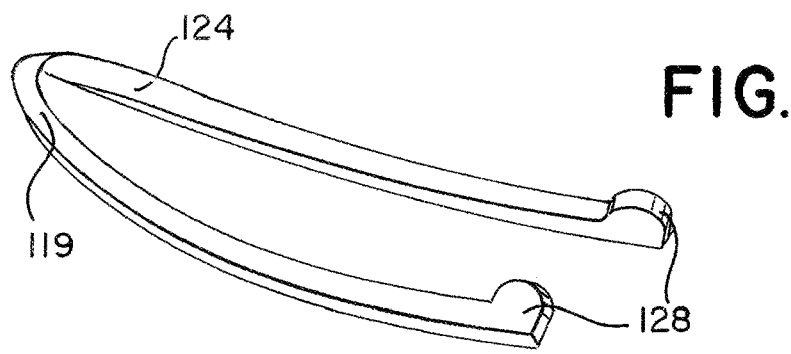
FIG. 6 shows an example of an actuated leaflet from the example from FIG. 4 according to aspects of the present invention.

In the example illustrated in FIGS. 4-6, the expansile tip 110 has six strut segments forming leaflets 124 with six distal peaks 119. Leaflets 124 can be laser cut integrally with the polymeric catheter shaft 220, machined as separate members (as seen in FIGS. 4-6), or a combination of integral and independent members. Adjacent leaflets 124 can circumferentially overlap at crossover points 126. The leaflets do not have to be fixedly coupled at the crossover points so that they are interlaced and can slide and fold relative to each other as the tip 110 expands or contracts. Designs having more than six leaflets can be appreciated where additional leaflet struts sacrifice some tip flexibility while providing additional radial force and support to prevent the collapse of the jackets or membrane (not shown). Similarly, fewer leaflets can be utilized in situations where a membrane of greater stiffness or thickness requires less support.

One or more pull cables 120 can extend along the length of the shaft 220 within the guide lumens 222 of the guide tubes 221. The pull cables 120 can be formed with distal loops 122 configured to encircle a crossover point 126 where two adjacent leaflets 122 overlap. When tensioned, the pull cables 120 can pull the crossover points 126 outward to increase the radial size and deploy the expansile tip 110. In some cases, the guide tubes 221 of the shaft 220 can have distal extensions 227 beyond the distal end 225 of the shaft.

Figure 9A:
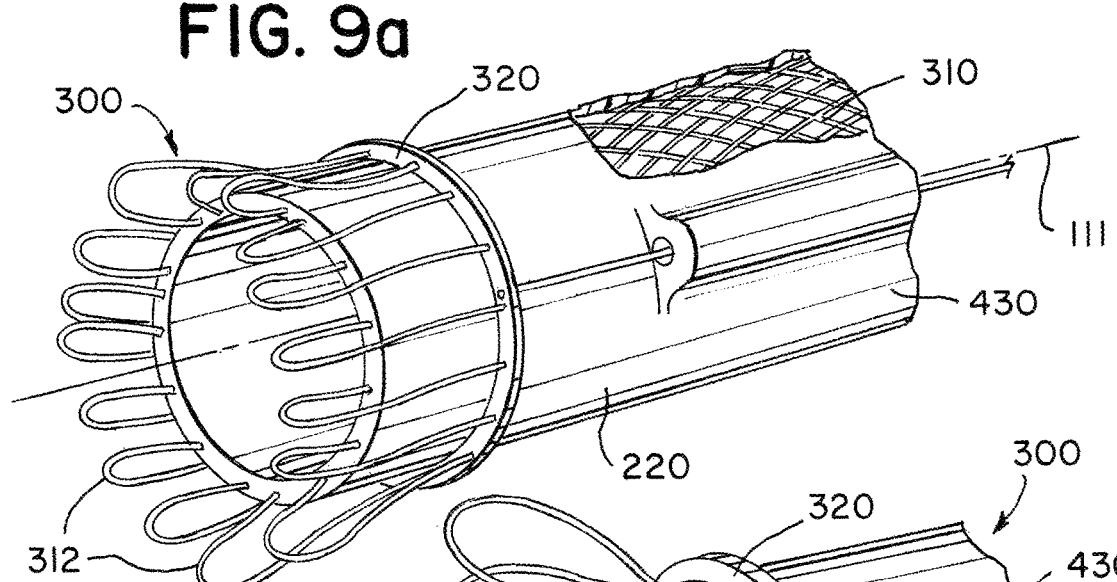
FIGS. 9*a*-9*b* show another alternative catheter example according to aspects of the present invention.

FIG. 5 illustrates the catheter shaft 220 of the catheter 100 of FIG. 4. Anchoring slots 226 can be located proximal to the distal end 225 of the shaft 220 so as to provide rigidity and retention to the proximal joint 114 between the shaft and the leaflets 124 of the distal tip 110. Independent adjacent leaflets 124, such as the example shown in FIG. 6, can have a hoop shape with a distal peak 119 and proximal feet or anchors 128. The leaflets 124 can be interlaced and their proximal leaflet anchors 128 laser welded or bonded together within the anchoring slots 226 of the shaft 220. In another example, some of the leaflets can be formed integrally with the shaft while other leaflets have anchors 128 that are welded or adhered onto the shaft. As another alternative, a collar circumscribing the distal end 225 of the shaft 220 can serve as a retaining ring to control the axial motion of the leaflet anchors 128 (an example of which is illustrated in FIG. 9a).

Figure 7:
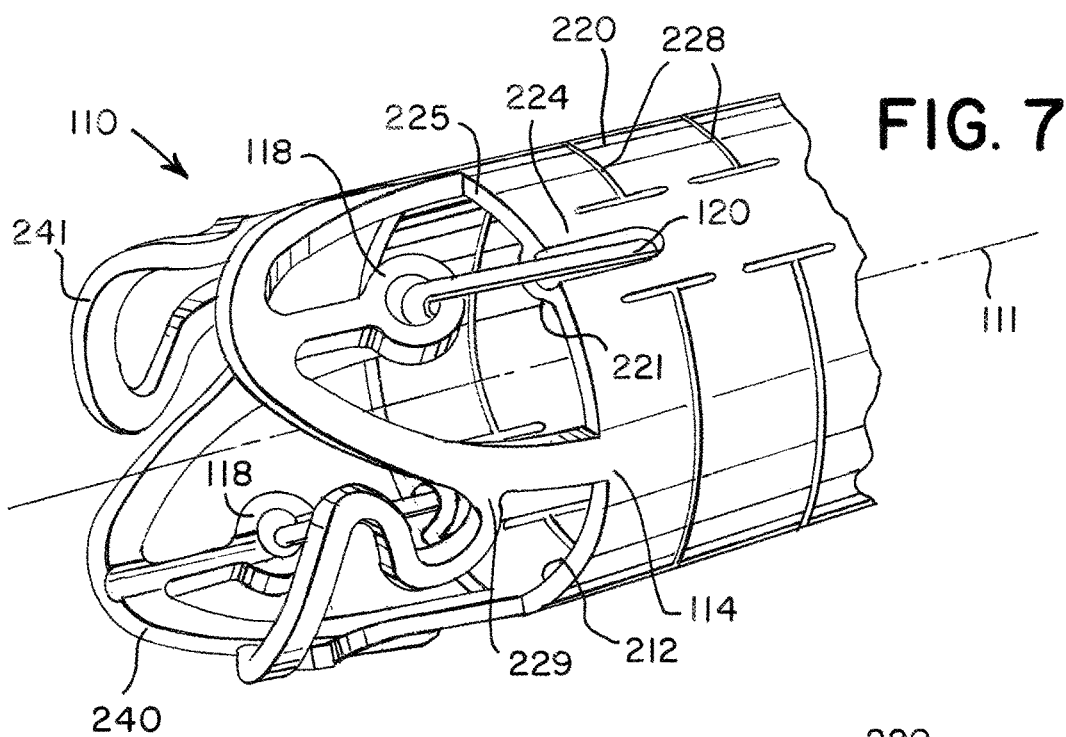
FIG. 7 shows another alternative catheter example according to aspects of the present invention.

The distal portion of another example of a thrombectomy catheter according to aspects of the invention is illustrated in FIG. 7. The tubular catheter shaft 220 can be formed from a polymeric extrusion. The extrusion can be, for instance, fabricated from polyether ether ketone (PEEK) or another rugged thermoplastic polymer. The extrusion can be configured with axial and/or transverse slots 228 cut into the outer surface to give additional lateral flexibility to the tubular shaft 220. The cuts can be longitudinally aligned or offset to tailor the stiffness properties for different axial sections of the shaft 220. The slots 228 can be circumferentially discontinuous so as to form one or more longitudinal spines 230 along the length of the shaft 220.

One or more pull cable guide tubes 221 can be disposed around the circumference of the catheter body 220 and can run the length of the catheter axis. The tubes 221 can be tangential and flush with the outer surface of the catheter tube or can be mid-wall or some other arrangement. As shown, some examples can have two pull cables spaced 180 degrees apart around the circumference of the catheter shaft, but other spaced arrangements can be anticipated when a greater number of cables is utilized. The guide tubes 221 may or may not be radially aligned with the one or more longitudinal spines 230, such that the tubes can serve as additional stiffening features if desired. Each guide tube can have an internal tubular lumen 212 sized to allow free relative axial motion of a pull cable 120. Similar to other designs, distal cutaways 224 can be provided to allow radial flexing of the pull cables 120 as tension is applied. The guide tubes can be rugged polymeric tubes offering good column stiffness and kink-resistance, such as polyimide tubing.

The funnel design of the expansile tip 110 of this example can be an integral lattice of leaflets 240, 241 laser cut directly with the catheter shaft 220. Alternately, the expansile tip 110 lattice can be injection molded as a single piece and attached to the shaft 220 by heat welding, adhesives, or similar means. The actuated leaflets 240 can be operably coupled with the pull cables 120 in a configuration similar to those described previously, such as knots, loops, or eyelets. The leaflets 240, 241 can be rounded distally with a gently sloping loop or petal shape for atraumatic contact with the walls of a vessel when expanded. The leaflets 240, 241 can contain bends such that they are capable or shortening and widening when the tip 110 is flared outwards as the pull cables 120 are retracted. As in other examples, a polymeric jacket or membrane can cover or encapsulate at least a portion of the tip 110 and catheter shaft 220.

FIG. 7 shows the expansile tip 110 in the collapsed delivery configuration. The tip 110 can include two actuation leaflets 240 and two passive leaflets 241 rigidly connected to the distal end 225 of the catheter shaft 220. The two passive leaflets 241 can be joined circumferentially to the actuated leaflets 240 at a circumferential joints 229, and the actuated leaflets can be fixedly connected to one of the pull cables.

The actuated leaflets 240 can account for a substantially larger portion of the circumference of the expansile tip 110 than the passive leaflets 241. As seen in FIG. 7, the passive leaflets 241 can have a substantially horseshoe shaped profile, where the legs of the horseshoe are circumferentially compressed together when the tip 110 is in the collapsed delivery configuration. The shape of the actuated leaflets 240 can be adjusted such that they shorten and widens (as well as flaring outwards) when pull cables 120 are retracted. This shape will help the neighboring passive leaflets 241 to flare out when pulled at the circumferential joints 229, thus making a more rounded funnel as opposed to being purely stretched into an ovular funnel shape.

Figure 8:
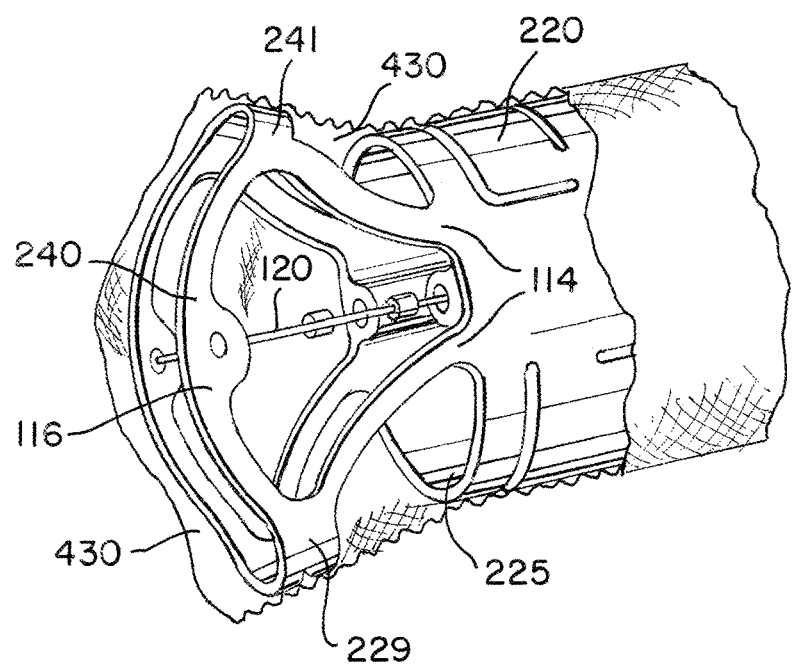
FIG. 8 illustrates an expanded profile of the example from FIG. 7 according to aspects of the present invention.

FIG. 7 is shown in the expanded deployed configuration in FIG. 8. The passive leaflets 241 can be shorter and intersect at circumferential joints 229 along the length of the actuated leaflets 240 so that the passive leaflets flare to a larger radial size. The combined flaring of all the leaflets contributes to a more rounded, uniform funnel better shaped to seal with a vessel, and to receive and compress a captured clot once it has been dislodged. In the example shown, the membrane or jacket 430 can be trimmed to follow the contours of the expanded mouth of the tip 110. In other examples, the jacket 430 can follow a squared or atraumatic concave profile.

Figure 9B:
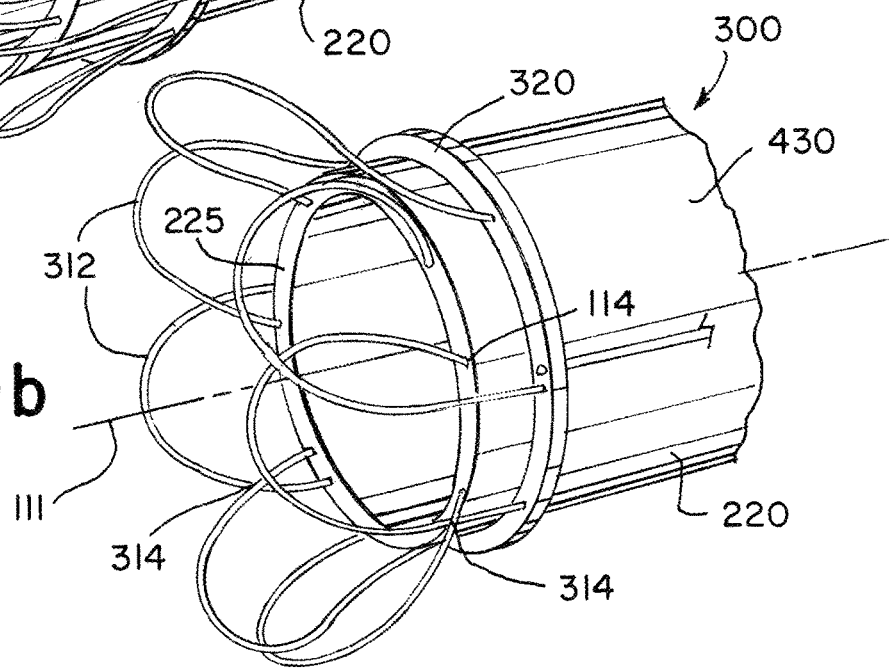

FIG. 9a and FIG. 9b show another configuration for a funnel-shaped catheter tip 300 where the leaflets are formed from a braided or coil weaved structure 310. The wires of the leaflets can form overlapping distal hoops 312 which can be interlaced and fixed in a sliding collar 320 that that can telescopically slide along the axis 111 of the catheter. The catheter body 220 can also have a woven or braided support structure which can form a tubular shape around a longitudinal axis 111. The density of the woven mesh could be configured so as to tailor local stiffness properties for axial sections of the catheter shaft 220. The distal hoops 312 can be integral with the wire braid 310 of the catheter, and the wire length and/or braid angle can be tailored so that when expanded, as shown in FIG. 9b, the hoops form a gentle funnel profile for the expanded tip 300.

In an example where the braided structure 310 of the expansile tip 110 and catheter shaft 220 can be formed integrally, the pull wires (not shown) can be looped around weave crossover points 314 for expansion of the tip 110 to the deployed configuration. In another example, the wires of the distal hoops can extend proximally to have a proximal joint 114 fixed directly to catheter body 220 or embedded within the outer polymeric jacket 430. The weave crossover points 314 of the distal hoops 312 can be kept as distal as possible. The distal hoops 312 can be free to move and slide with respect to each other.

The braided mesh can be of metallic wire construction, and can utilize alloys with shape memory properties, such as Nitinol. To form the braided mesh, a one-piece wire can be wrapped around forming tool with a tapered, bullet-shaped nose to heat set the tip in a distally-reducing outer diameter for atraumatic crossing within a blood vessel. To impart increased stiffness to the wire to aid in opening an elastomeric membranes, the wire outer diameter can be relatively large. In one example, the outer diameter of the wire could be in the range of 0.004" to 0.008". In order to maximize flow rate and the proximal cross-section of the tip for reception of clot, the segments of the wire can be flattened with a press tool. The distal sections of the wire forming the expansile tip that opens when actuated can also be flattened, but this section can also be left round as the increased diameter of the tip in the expanded deployed state will not impact the cross-section.

Figure 10:
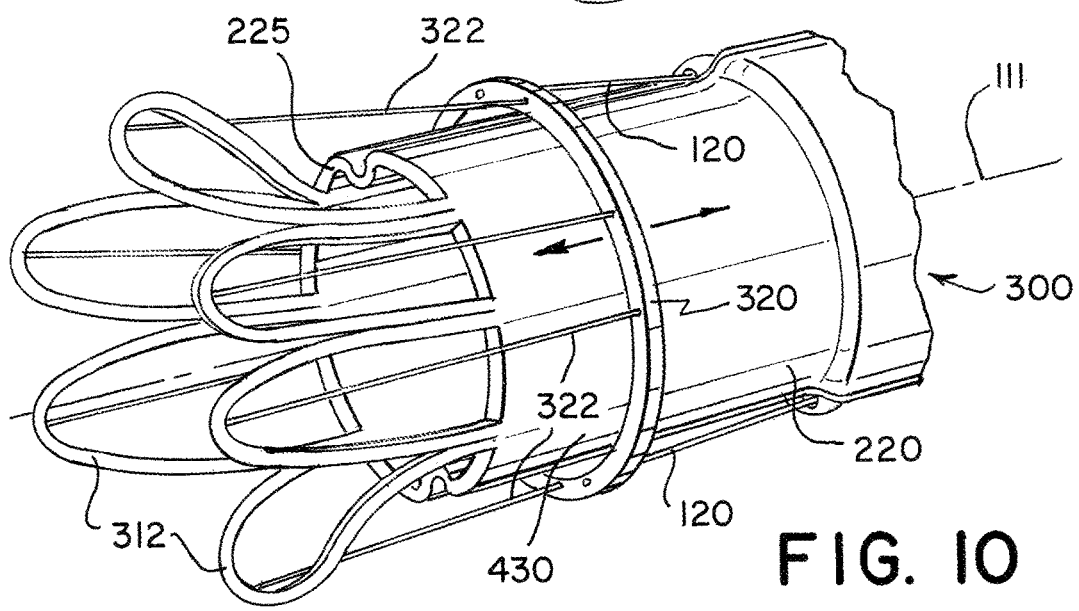
FIG. 10 illustrates a possible activation of the tip of the example from FIGS. 9*a*-9*b* according to aspects of the present invention.

An example of the actuation mechanism of the tip example shown in FIGS. 9a to the deployed configuration is illustrated in FIG. 10. A collar 320 can be slidably disposed around at least a portion of the catheter shaft 220 and configured to translate along the longitudinal axis 111 of the catheter through the tensioning or pushing of the one or more pull cables 120. The distal hoops 312 can have hoop tensioning members 322 connected to the sliding collar 320. The tensioner members 322 can be wire or strip and can connect to some or all of the hoops 312 of the braided structure 310 of the expansile tip 300. The tensioning members 322 can then flare and expand the tip when the collar 320 is pulled proximally with the pull cables 120. The strands of the distal hoops 312 can be embedded in or otherwise connected to the shaft 220, such that they radially expand when the collar pulls translated proximally. The pull force can be evenly distributed to the hoops 312 through two pull cables 120 spaced 180 degrees apart.

As an alternative, at least a portion of the outer jacket or membrane 430 can be inverted over the expansile tip 110 and bonded to the slidable collar 320. The membrane 430 can extend radially inward of the hoops 312 to be bonded to the inner diameter of the shaft 220. The membrane 430 can then radially expand the hoops 312 when the collar 320 is pulled proximally with the pull cables 120.

It should be noted that any of the herein disclosed catheters designs can also be used with one or more stentrievers. The combined stentriever retraction and efficient aspiration through the enlarged tip section in the expanded deployed configuration can act together to increase the likelihood of first pass success in removing a clot. The catheter can also direct the aspiration vacuum to the clot face while the stentriever will hold a composite clot (comprised of friable regions and fibrin rich regions) together preventing embolization and aid in dislodging the clot from the vessel wall. The funnel-like shape of the tip section can also reduce clot shearing upon entry to the catheter and arrest flow to protect distal vessels from new territory embolization.

Figure 11A:
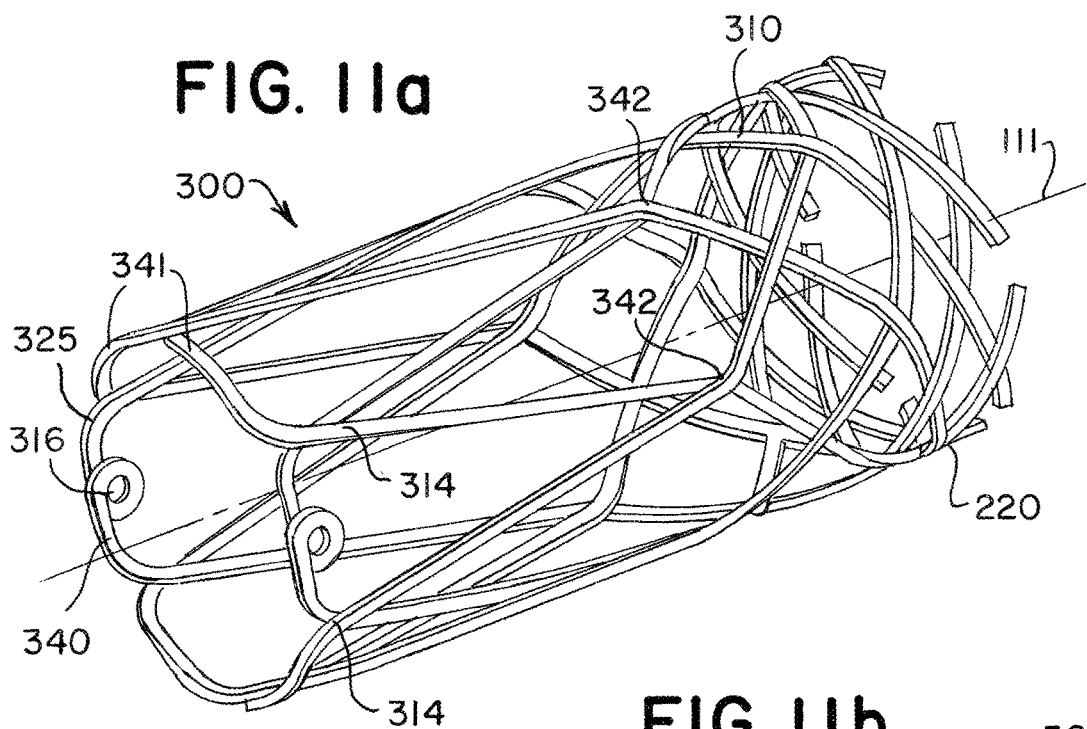
FIGS. 11*a*-11*b* depict another alternative catheter example according to aspects of the present invention.
Figure 11B:
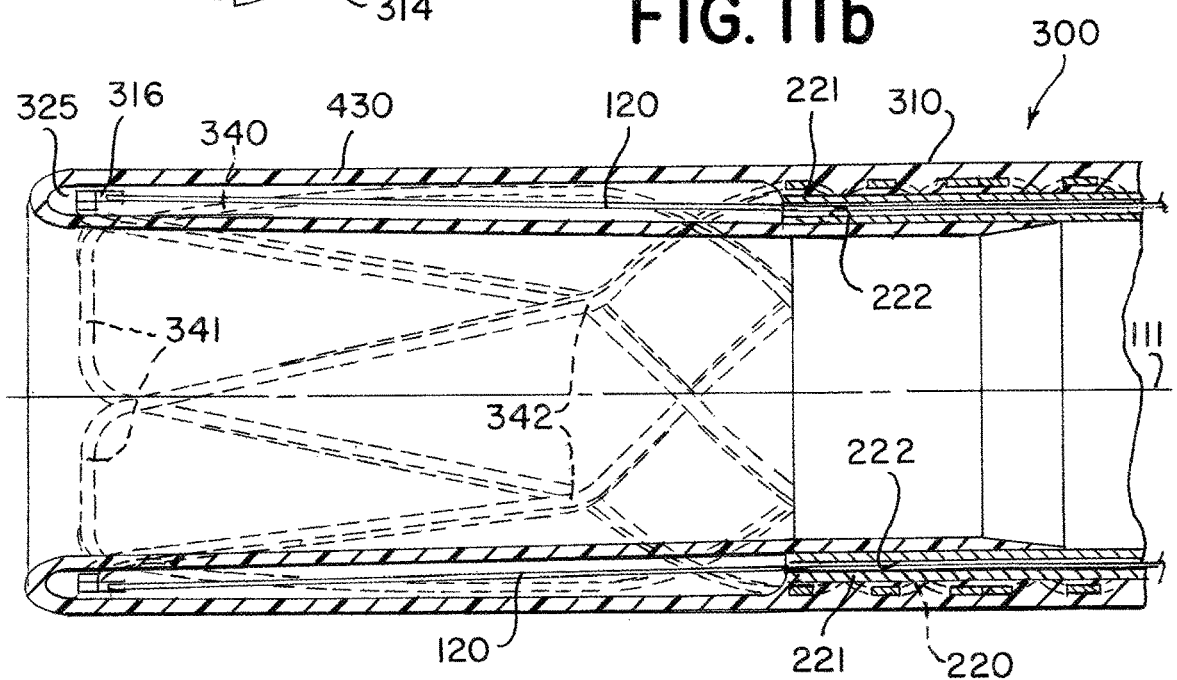

FIG. 11a and FIG. 11b illustrate an additional configuration for a funnel-shaped catheter tip 300 where the leaflets are formed from a braided or coil weaved structure 310. The braided structure 310 of the tip 300 can be integral with that of the catheter shaft 220. The pattern of the braid 310 can allow the actuation of the tip from two pull wires 120 to transmit force from diametrically opposed actuated leaflets 340 to adjacent passive leaflets 341 so that all the leaflets move from a substantially tubular collapsed delivery condition as shown to an open deployed configuration for aspiration and/or the delivery of devices. In one example, the pull wires 120 can be attached to braid loops or eyelets 316 at the distal end 325 of the actuated leaflets 340. In another example, the pull wires 120 can simply be welded to the middle of the distal end 325 of the actuated leaflets 340 or attached at weave crossover points 314.

As depicted in FIG. 11a, the actuated leaflets 340 can be positioned under (radially inboard) each of the adjacent passive leaflets 341 such that tensioning the pull wires (not shown) can open all the leaflets in a balanced manner. Proximally, the struts of the leaflets 340, 341 can each have a single twist at crossover leaflet twist points 342 which can help anchor the leaflets with respect to one another and serve as a pivot for radial expansion of the tip 300. Alternatively, a spot weld between the leaflets at the twist points 342 can secure the location. An advantage of this configuration is that when the expandable tip is opened, the connection between the pull wires and the actuated leaflets does not need to be slidable since the leaflets 340, 341 can slide with respect to one another at the crossover points 314.

In another configuration, the pull wires 120 of the tip 300 can be looped over the distal leaflet crossover points 314 similar to the expansile tip seen in FIG. 4. This configuration allows the tension in the pull wires to be more evenly translated to the expanding leaflets. In this configuration the actuated leaflets 340 can be positioned over (radially outboard) or under (radially inboard) of the adjacent passive leaflets 341. The pull wire attachment at the crossover points 314 must be slidable, however, to allow the crossover points to slide to a more proximal position as the leaflets are radially expanded.

The braid weave 310 can be covered with a membrane or outer jacket 430 as illustrated in FIG. 11b. The jacket 430 can extend distally under the leaflets 340, 341 of the tip 300 from the inner diameter of the catheter and invert at the distal end 325 to extend proximally over the leaflets. As an inverted jacket 430 does not need to be adhered to the tip with this design, the leaflets are free to move relative to one another inside the inverted jacket sock.

Similar to previous examples, pull cable guide tubes 221 can extend longitudinally with the catheter shaft 220. In some examples, the pull cables 120 can extend from the guide tubes distally under the braid leaflets 340, 341. This orientation would make the catheter easier to assemble, at the cost of reducing the tensile leverage for actuation of the tip 300 as the twist points 342 can restrict the radial movement of the pull cables 120 as the tip is expanded. In other examples, the leverage for the actuated expansion of the tip can be retained by threading the pull cables 120 over the leaflets 340, 341 so that there is no restriction as the pull cables exit the guide tubes 221. This configuration can allow for a higher opening force to be generated, but assembly of the catheter can be more difficult than if the pull cables were threaded beneath the leaflets.

Figure 12A:
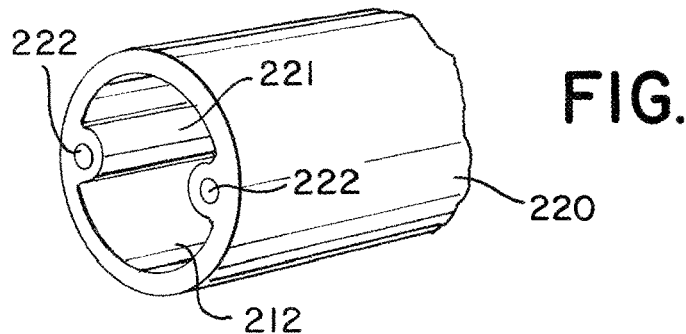
FIG. 12*a* is an end view of a single extrusion catheter shaft construction according to aspects of the present invention.

Various methods of manufacture can be employed to produce the examples catheters disclosed herein. FIGS. 12a-12b show transverse end views of possible construction methods for the catheter shaft 220 of the clot retrieval catheter. In FIG. 12a, the shaft could be a one-piece multi-lumen extrusion which is then laser cut to add flexibility. For example, the shaft 220 can have spiral-cut sections between the proximal end to the distal end. The cuts can include variations in cut width so that a longitudinally-aligned series of narrow transverse slots can form one or more axial spines 230 parallel to the guide tubes 221 in the extrusion. Axial spines can give the shaft good pushability while maintaining the flexibility of the shaft. The multi-lumen shaft 220 can have twin guide tubes 221 having pull cable lumens 222 spaced 180 degrees apart. At least one of the twin pull cable lumens 222 can also have an internal tether (not shown) extending therethrough to prevent excessive elongation of the shaft in tension. In one example, the tether or tethers can be made of a fluoropolymer or other material that gives resistance to stretch. Limited stretch allows the cuts in the extrusion to open when the shaft 220 is in tight radii in the vascular. The tethers can also resist the cuts from pulling apart substantially under more significant tensile forces such as in cases where the expansile tip needs to be retracted into an outer sheath or intermediate catheter when a stiff, fibrin-rich clot is lodged in the tip.

In one example, the catheter can have a shaft having an inner surface and an outer surface, with the perimeter of the inner surface being greater than the perimeter of the outer surface. Although illustrated as tangent to and traversing the inner wall of the extrusion, it can be appreciated that the pull cable guide tubes 221 and lumens 222 could also be located mid-wall or external to the outer wall of the extrusion.

The extrusion can be a high-modulus thermoplastic polymer, such as PEEK, Polyamide (Pa), or a Nylon such as TR 55 to give the shaft excellent pushability performance. In addition, the extrusion material could be a high-modulus and low-friction polymer to aid in the passage of other devices for the procedure, such as microcatheters, stentrievers, and guidewires. A heat-shrunk outer jacket or membrane 430 (not shown) can seal the shaft 220 extrusion when fused to the outer diameter the shaft.

In another example, a low friction layer or film could be applied to the inner diameter of the shaft 220 through the use of an undersized PTFE or other low-friction liner with an outer strike layer for bonding which can be positioned inside the extrusion. A heated mandrel with an enlarged end can be then drawn through the liner to expand and adhere the liner to the inner surface of the laser cut extrusion. Additional heat could be applied to the extrusion as necessary for the liner to fuse.

FIG. 12b shows an alternative shaft 220 of a layered, composite construction. The layers can include a low-friction inner sleeve or liner 410 and a tubular core 420 over which the outer jacket or membrane 430 can be applied. The core could be an extrusion, a laser cut hypotube, or a coiled or braided mesh to provide structure and reinforcement for the catheter shaft 220.

Figure 13D:
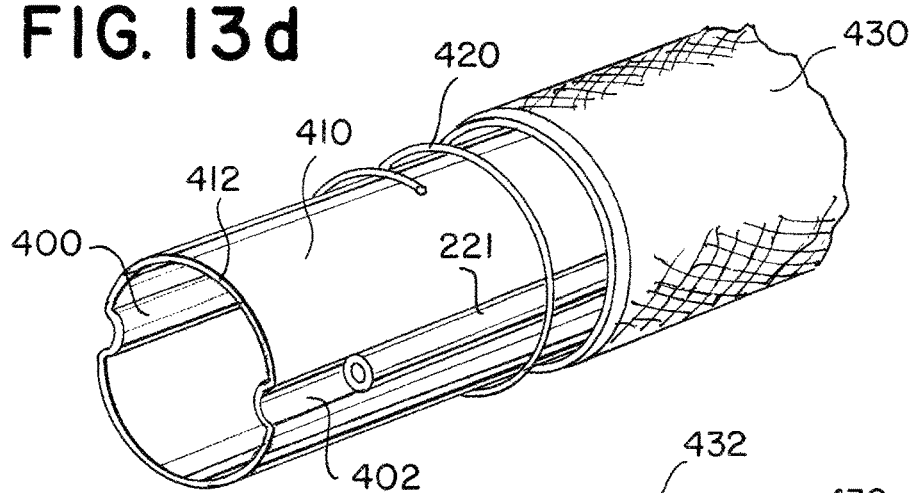

A composite layered catheter shaft 220 can be described through a method for construction as illustrated in FIGS. 13a-13d. In FIG. 13a, a substantially cylindrical mandrel 400 can be fabricated which can have an outer diameter which is approximately the same as the desired inner diameter of the catheter shaft 220. The mandrel 400 can have one or more longitudinal lumen grooves 402 machined into the outer surface parallel to the longitudinal axis 111 to serve as a mold for the pull wire guide tubes 221.

In FIG. 13b, the composite construction can include a flexible inner layer 410 having low-friction liner 411 such as PTFE or PET and a thick strike layer 412 bonded to the low-friction liner. The flexible inner layer 410 can be assembled as a sleeve over the cylindrical mandrel 400. In FIG. 13c, polyamide or similar tubes forming the lumen guide tubes 221 can be inserted into the lumen grooves 402 of the mandrel 400 to press the inner layer 410 into the grooves. A coil or braided reinforcing layer 420 can then be wrapped or disposed around the outer diameter of the inner layer 410 and guide tubes 221. As mentioned previously, the pitch or axial spacings of the coil or braid reinforcement 420 can be varied to tailor the stiffness properties for different axial lengths of the catheter shaft 220. The reinforcing coil 420 can tie the guide tubes 221 securely to the inner layer 410. In other examples, a laser cut tube can be used in place of the coil or braid and slid over the assembly to hold the mandrel 400, inner layer 410, and guide tubes 221 together.

As used herein, the terms jacket, membrane, and cover are used interchangeably. The outer jacket or membrane 430 can be applied over the top of the composite construction and reflowed using heat shrink or laminated to hold the assembly together. In some instances, the jacket can be of several sections with varying material properties. In FIG. 13d, once the jacket or membrane 430 is secured, the grooved mandrel 400 can be removed.

Figure 14:
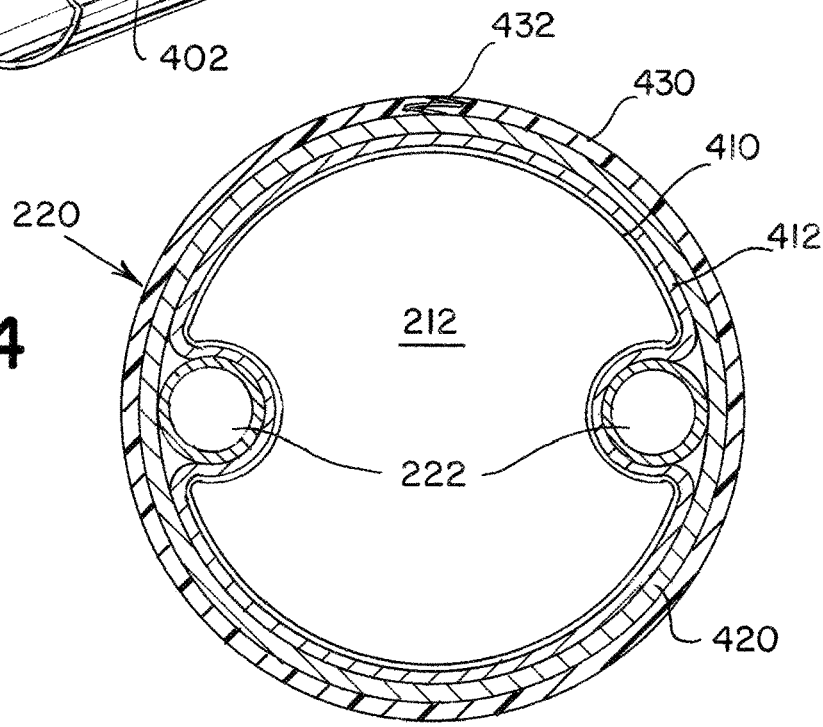
FIG. 14 is a cross-section view of a composite catheter shaft construction according to aspects of the present invention.

FIG. 14 is a cross-section view of the composite catheter shaft 220 construction which can result from the method of FIGS. 13a-13d. The outer jacket can be a membrane cover 430 and can take a variety of different forms or configurations as further described. The membrane or cover can be formed in a tubular profile with a highly elastic material such that expansion of an expansile tip will impart a sufficient radial force to stretch the cover when unconstrained. The cover 430 can also be pre-formed in a tapered funnel shape with pleats or creases 432 allowing it to fold into a lower-profile for delivery.

Suitable jacket materials can include elastic polyurethanes such as Chronoprene, which can have a shore hardness of 40A or lower, or silicone elastomers. If the catheter shaft 220 and tip framework are formed from a polymeric extrusion, spaces, slots, or patterns can be laser-cut into the outer surface and the jacket can be reflowed or injection molded into the spaces during manufacturing. Alternately, the jacket can be laminated to the structure.

In order to allow for smooth delivery of the clot retrieval catheter 100 through an outer catheter, the outer surface of the membrane 430 can be coated with a low-friction or lubricious material, such as PTFE or commercially available lubricious coatings such as offered by Surmodics, Harland, Biocoat or Covalon. Similarly, the inner surface of the catheter shaft 220 can also be coated with the same or similar low-friction material for the passage of auxiliary devices and to aid in a captured clot being drawing proximally through the catheter 100 with aspiration and/or a mechanical thrombectomy device.

In other examples, the jacket or membrane can be a straight extrusion or extruded and post-formed onto the expansile tip and catheter body. As an alternative, in cases where the catheter shaft and expansile tip have a laser cut strut, coil, or braided structure, the structure can be encapsulated within the membrane as part of a dip coating or plasma deposition process.

The cover can be trimmed to follow the contours of the mouth of the expansile tip along the perimeter of the mouth or it can be finished with a planar face. In another example, the cover membrane can be folded radially inward and proximal of the distal peaks of the leaflets and heat welded between the inner and outer layers. The thickness of the cover can be maintained between and over the leaflets of the tip or it can be finished with a uniform thickness.

Figure 15A:
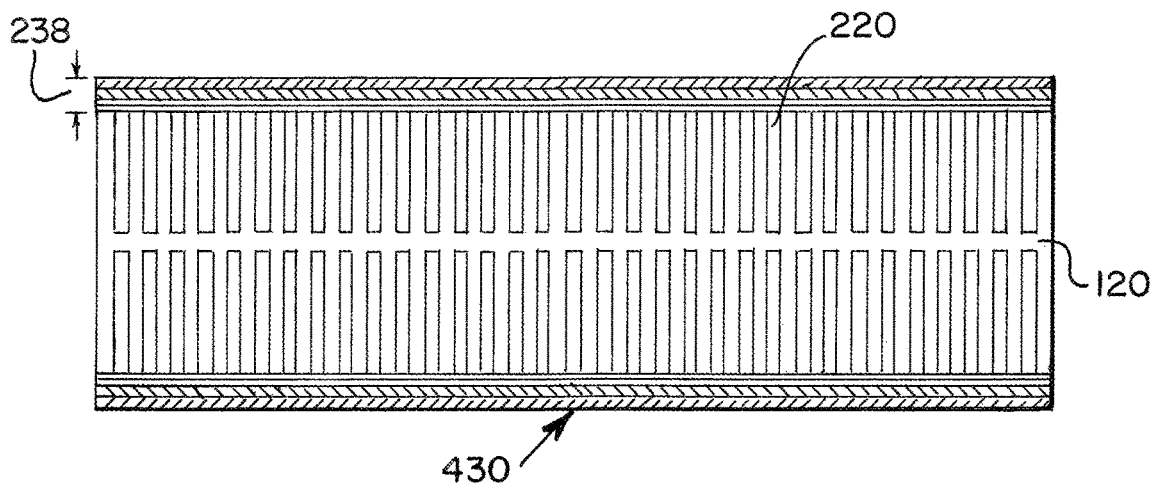
FIGS. 15a-15b shows longitudinal sections of the catheter shaft with alternative membrane arrangements according to aspects of the present invention.
Figure 15B:
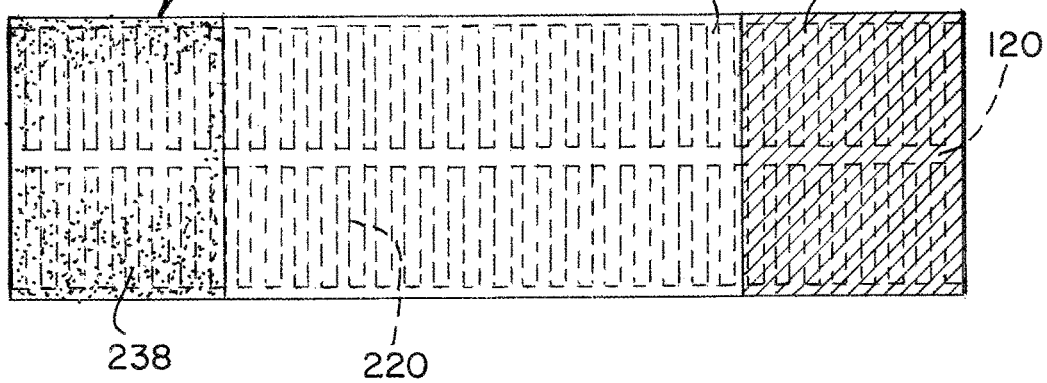

As an alternative, the jacket or membrane 430 can also be a formed from a series of layers of polymer jackets 238, as illustrated in FIGS. 15a-b. For example, the polymer jackets 238 of the cover can be in a radial series disposed about the catheter shaft 220 in order to tailor the material properties through the thickness, as shown in FIG. 15*a*. Alternately, different durometer jackets or sets of jackets 238 can be disposed around the catheter shaft 220 at discrete lengths along the axis in order to give distinct pushability and flexibility characteristics to different sections of the catheter as shown in FIG. 15*b*. By configuring the jackets in an axial series, it is possible to transition the overall stiffness of the catheter from being stiffer at the proximal end to extremely flexible at the distal end.

The series of polymer jackets 238 can be butted together and fused to the catheter shaft 220. The expansile tip can have the same or a separate jacket or jackets that can be dip coated and can butt against or situated under or over the jacket or jackets of the catheter shaft. If the jacket of the tip is under the jackets of the shaft, it can be manufactured from a material capable of withstanding the heat generated when the jackets of the support tube are reflowed. In a further example, an outer jacket pre-formed with variable stiffness and elasticity characteristics can be substituted for the series of polymer jackets.

Figure 16A:
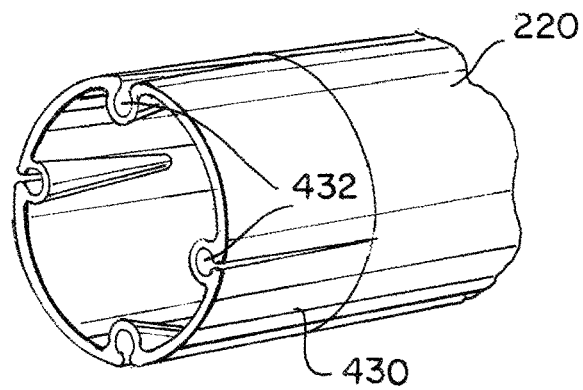
FIGS. 16a-16d are examples showing alternative ways of disposing the membrane cover on the expansile tip according to aspects of the present invention.
Figure 16B:
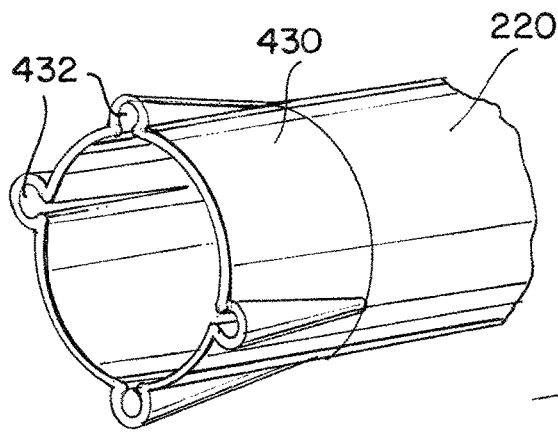

FIGS. 16*a*-16*d* briefly show several examples of how the jacket 430 can be disposed around an unexpanded tip 110 towards the distal end of the catheter shaft 220. FIGS. 16*a*-16*b* show cases where the jacket 430 has been applied with creases or pleats 432 to allow folding for a low-profile delivery state in situations where an oversized or baggy jacket is employed. The pleats 432 can then unfold when the tip 110 is expanded to the deployed configuration. The jacket 430 can overlap the expanded petals or leaflets of the tip to extend the circumference and minimize the strain imparted on the jacket as the tip expands. In a similar example, the jacket 430 can be only slightly oversized for the expansile tip and a combination of unfolding pleats 432 and elastic expansion of the jacket are used to conform the jacket to the contours of the expanded tip.

Figure 16C:
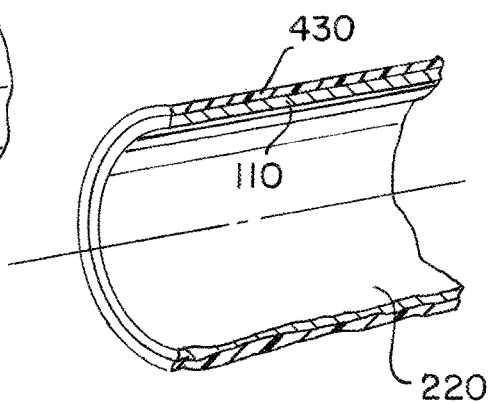
Figure 16D:
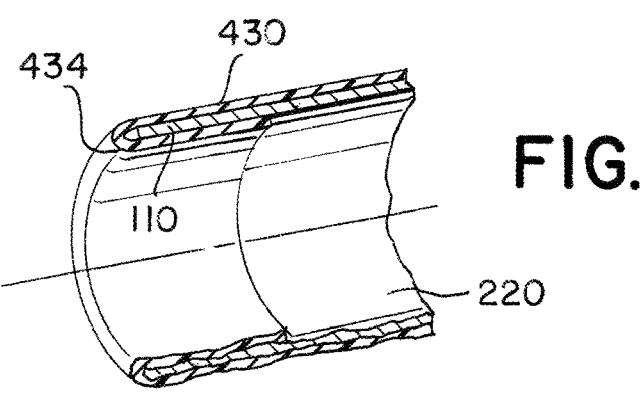

FIG. 16*c* shows a profile sectioned view of the distal portion of the catheter 100 with a covering membrane 430 applied over an expansile tip 110. The membrane 430 could dipped or deposited with a plasma process and subsequently laminated to the frame. The membrane edge could be trimmed to follow the distal edges of the tip 110 or left as a planar face. In a separate example shown in FIG. 16*d*, the membrane 430 could be allowed to fold over or invert around the frame of the tip 110 so that a soft, atraumatic lip 434 is created. The membrane 430 could either be fused to the tip 110 or the tip structure could be configured to slide freely within the lip 434.

The invention is not necessarily limited to the examples described, which can be varied in construction and detail. The terms "distal" and "proximal" are used throughout the preceding description and are meant to refer to a positions and directions relative to a treating physician. As such, "distal" or "distally" refer to a position distant to or a direction away from the physician. Similarly, "proximal" or "proximally" refer to a position near to or a direction towards the physician. Furthermore, the singular forms "a," "an," and "the" include plural referents unless the context clearly dictates otherwise.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90°" may refer to the range of values from 71% to 99%.

In describing example embodiments, terminology has been resorted to for the sake of clarity. It is intended that each term contemplates its broadest meaning as understood by those skilled in the art and includes all technical equivalents that operate in a similar manner to accomplish a similar purpose without departing from the scope and spirit of the invention. It is also to be understood that the mention of one or more steps of a method does not preclude the presence of additional method steps or intervening method steps between those steps expressly identified. Some steps of a method can be performed in a different order than those described herein without departing from the scope of the disclosed technology. Similarly, it is also to be understood that the mention of one or more components in a device or system does not preclude the presence of additional components or intervening components between those components expressly identified. For clarity and conciseness, not all possible combinations have been listed, and such modifications are often apparent to those of skill in the art and are intended to be within the scope of the claims which follow.

What is claimed is:

1. A thrombectomy catheter, the catheter comprising:
 a tubular catheter shaft comprising:
  a distal end and a catheter lumen with a longitudinal axis extending therethrough;
  one or more pull cable guide tubes comprising pull cable lumens disposed about the circumference of the catheter lumen and extending the longitudinal length of the catheter shaft; and
  one or more pull cables disposed within the pull cable lumens and capable of being operably tensioned by a user of the catheter; and
 an expansile tip having a collapsed delivery configuration and a radially expanded deployed configuration, the expansile tip comprising one or more leaflets around the longitudinal axis and configured to assume a funnel profile when the expansile tip is in the expanded deployed configuration;
 wherein the one or more pull cables are configured to actuate the expansile tip between the collapsed delivery configuration and the expanded deployed configuration when a tensile force is applied to the pull cables,
 wherein the plurality of leaflets comprise one or more actuated leaflets and one or more passive leaflets,
 wherein the one or more actuated leaflets and one or more passive leaflets comprise looped struts comprising a distal peak and one or more proximal joints connected to the catheter shaft,
 wherein each of the one or more actuated leaflets further comprise tensioning members extending proximally from the distal peak of the leaflets and fixedly connected to pull cables, and
 wherein the pull cables comprise bulbs connected to eyelets of the tensioning members.

2. The catheter of claim 1, wherein the actuated leaflets and passive leaflets are configured to slide on each other as the expansile tip transitions between the collapsed delivery configuration and the radially expanded deployed configuration.

3. The catheter of claim 1, the catheter shaft further comprising one or more distal cutaways from the pull cable guide tubes approximate the distal end, the one or more distal cutaways configured to allow the pull cables to exit the pull cable lumens at a shallow angle to the longitudinal axis.

4. A thrombectomy catheter, the catheter comprising:
 a tubular catheter shaft comprising:

a distal end and a catheter lumen with a longitudinal axis extending therethrough; and one or more pull cable guide tubes disposed about the circumference of the catheter lumen, the guide tubes having one or more pull cables disposed within pull cable lumens and capable of being operably tensioned by a user of the catheter; and an expansile tip integrally formed at the distal end of the catheter shaft, the expansile tip comprising a plurality of leaflets configured to radially expand from a collapsed delivery configuration to an expanded deployed configuration when the one or more pull cables are tensioned, wherein the plurality of leaflets comprise one or more actuated leaflets and one or more passive leaflets, wherein the one or more actuated leaflets and one or more passive leaflets comprise looped struts comprising a distal peak and one or more proximal joints connected to the catheter shaft, wherein each of the one or more actuated leaflets further comprise tensioning members extending proximally from the distal peak of the leaflets and fixedly connected to the pull cables, and wherein the pull cables comprise bulbs connected to eyelets of the tensioning members.

5. The catheter of claim 4, wherein the one or more pull cables comprise two pull cables spaced 180 degrees apart around the circumference of the catheter shaft.

6. The catheter of claim 5, wherein the plurality of leaflets comprise two actuated leaflets and two passive leaflets joined circumferentially to the actuated leaflets, each of the actuated leaflets being fixedly connected to one of the two pull cables; and the actuated leaflets are configured to actuate the expansile tip between the collapsed delivery configuration and the expanded deployed configuration when the pull cables are tensioned.

7. The catheter of claim 6, wherein the passive leaflets comprise a substantially horseshoe shaped profile.

8. The catheter of claim 6, wherein the actuated leaflets comprise a substantially larger portion of the expansile tip circumference than the passive leaflets.

\* \* \* \* \*